(12) United States Patent
Shenderova et al.

(10) Patent No.: US 10,287,495 B1
(45) Date of Patent: *May 14, 2019

(54) PHOTOLUMINESCENT NANODIAMOND MATERIAL

(71) Applicant: International Technology Center, Raleigh, NC (US)

(72) Inventors: Olga Alexander Shenderova, Raleigh, NC (US); Igor Vlasov, Zukovskii (RU); Suzanne Ani-Ciftan Hens, Durham, NC (US); Vesna Borjanovic, Cary, NC (US)

(*) Notice: Subject to any disclaimer, the term of this patent is extended or adjusted under 35 U.S.C. 154(b) by 306 days.

This patent is subject to a terminal disclaimer.

(21) Appl. No.: 14/978,184

(22) Filed: Dec. 22, 2015

Related U.S. Application Data

(60) Division of application No. 12/660,457, filed on Feb. 26, 2010, now Pat. No. 9,260,653, which is a continuation-in-part of application No. 11/990,948, filed as application No. PCT/US2006/033626 on Aug. 25, 2006, now Pat. No. 9,296,656.

(60) Provisional application No. 61/233,950, filed on Aug. 14, 2009, provisional application No. 61/162,457, filed on Mar. 23, 2009, provisional application No. 61/156,571, filed on Mar. 2, 2009, provisional application No. 60/712,507, filed on Aug. 30, 2005.

(51) Int. Cl.
| | |
|---|---|
| C09K 11/65 | (2006.01) |
| C09K 11/56 | (2006.01) |
| C09K 11/06 | (2006.01) |
| C09K 11/08 | (2006.01) |
| A61K 47/02 | (2006.01) |

(52) U.S. Cl.
CPC ............. *C09K 11/65* (2013.01); *A61K 47/02* (2013.01)

(58) Field of Classification Search
None
See application file for complete search history.

(56) References Cited

U.S. PATENT DOCUMENTS

| | | |
|---|---|---|
| 4,483,836 A | 11/1984 | Adadurova et al. |
| 4,799,963 A | 1/1989 | Basil et al. |
| 5,861,349 A | 1/1999 | Verschagin et al. |
| 5,866,059 A | 2/1999 | Fujiwara et al. |
| 6,264,859 B1 | 7/2001 | Basil et al. |

(Continued)

FOREIGN PATENT DOCUMENTS

| | | |
|---|---|---|
| DE | 199 33 648 A1 | 1/2001 |
| KR | 2004 105096 | 12/2004 |
| WO | WO 2007027656 | 3/2007 |

OTHER PUBLICATIONS

Office Action for U.S. Appl. No. 12/820,230, dated Jul. 9, 2013.

(Continued)

*Primary Examiner* — Ronak C Patel
(74) *Attorney, Agent, or Firm* — James G. Passé

(57) ABSTRACT

Photoluminescent nanodiamond particles of dynamic synthesis have enhanced photoluminescent properties produced as a result of minimizing the nitrogen content of impurities or imperfections in the nanodiamond lattice and by location of photoluminescent structures on the outer surface of the nanodiamond particles. This inhibits suppression (i.e. inactivity) of emission and enhances the intensity of the emission. This abstract is not to be considered limiting, since other embodiments may deviate from the features described in this abstract.

35 Claims, 8 Drawing Sheets

(56) References Cited

U.S. PATENT DOCUMENTS

| | | |
|---|---|---|
| 6,455,442 B1 | 9/2002 | Bauer et al. |
| 7,224,039 B1 | 5/2007 | McGuire et al. |
| 2004/0016397 A1 | 1/2004 | Carlson et al. |
| 2004/0202601 A1 | 10/2004 | Wen et al. |
| 2005/0008560 A1 | 1/2005 | Kataoka et al. |
| 2005/0158549 A1 | 7/2005 | Khabashesku et al. |
| 2006/0241236 A1* | 10/2006 | Kuznetsov ............... C09D 7/61 524/495 |
| 2008/0113448 A1 | 5/2008 | Sun |
| 2008/0118966 A1 | 5/2008 | Chang et al. |
| 2009/0220556 A1 | 9/2009 | Shenderova et al. |
| 2009/0297828 A1 | 12/2009 | Shenderova et al. |
| 2010/0068503 A1 | 3/2010 | Neogi et al. |
| 2010/0179075 A1* | 7/2010 | Lau .................. G01N 33/54393 506/32 |
| 2010/0190007 A1 | 7/2010 | Wu |
| 2010/0278712 A1 | 11/2010 | Swanson |
| 2010/0285304 A1 | 11/2010 | Wu |
| 2010/0305309 A1* | 12/2010 | Ho ........................ C07K 17/14 530/402 |

OTHER PUBLICATIONS

Carbon Based Nanostructures: Diamond Clusters Structured with Nanatubes, Shenderova et al., Sep. 2002.

Office Action for U.S. Appl. No. 12/820,230 filed Jun. 22, 2010, dated Jan. 3, 2013.

Ay et al, "The Physicochemical and Electrochemical Properties of 100 and 500 nm Diameter Diamond Powders Coated with Boron-Doped Nanocrystalline Diamond," May 5, 2008, Journal of the Electrochemical Society, 155 (10), pp. B1013-B1022.

Alexios Beveratos et al., "Nonclassical Radiation from Diamond Nanocrystals," Physical Review A, vol. 64, pp. 061802-1-061802-4, 2001.

Vesna Borjanovic et al., "Effect of Proton Irradiation on Photoluminescent Properties of PDMS—Nanodiamond Composites," Nanotechnology 19, 2008.

I. Cabria et al., "Interaction of Narrow Carbon Nanotubes with Nitronium Tetrafluoroborate Salts," The Journal of Chemical Physics 128, pp. 214703-1-214703-8, 2008.

L. C. Huang et al., "Adsorption and Immobilization of Cytochrome c on Nanodiamonds," Langmuir 20, pp. 5879-5884, 2004.

S.C. Ray et al., "Fluorescent Carbon Nanoparticles: Synthesis, Characterization and Bioimaging Application," Journal of Physical Chemistry C, 113, pp. 18546-18551, 2009.

Olga Shenderova et al., U.S. Appl. No. 12/592,354, filed Nov. 24, 2009.

Ya-Ping Sun et al., "Doped Carbon Nanoparticles as a New Platform for Highly Photoluminescent Dots," The Journal of Physical Chemistry Letters 112, pp. 18295-18298, 2008.

Xin Wang et al., "Photoinduced Electron Transfers with Carbon Dots,"Chemical Communication, pp. 3774-3776, 2009.

Xiaoyou Xu et al, "Electrophoretic Analysis and Purification of Fluorescent Single-Walled Carbon Nanotube Fragments," Journal of American Chemical Society 126, pp. 12736-12737, 2004.

Weng Siang Yeap et al., "Using Detonation Nanodiamond for the Specific Capture of Glycoproteins," Analytical , Chemistry vol. 80, No. 12, pp. 4659-4665, 2008.

Shu-Jung Yu et al., "Bright Fluorescent Nanodiamonds: No Photobleaching and Low Cytotoxicity," Journal of American , Chemical Society 127, pp. 17604-17605, 2005.

F. Zelezko et al, "Single Defect Centres in Diamond: A Review," Phys. Stat. Sol. (a) 203, No. 13, pp. 3207-3225, 2006.

Gaixia Zhang et al., "The Surface Analytical Characterization of Carbon Fibers Functionalized by H2SO4/HNO3 Treatment," Science Direct, Carbon 46, pp. 196-205, 2008.

\* cited by examiner

PHOTOLUMINESCENT NANODIAMOND MATERIAL

CROSS REFERENCE TO RELATED DOCUMENTS

This application is a divisional application of U.S. patent application Ser. No. 12/660,457 (ITC-P25) filed Feb. 26, 2010 which is a continuation-in-part of U.S. patent application Ser. No. 11/990,948, filed Feb. 25, 2008 via PCT application PCT/US2006/033626 filed Aug. 25, 2006, which claims priority benefit of U.S. Provisional Patent Application No. 60/712,507 filed Aug. 30, 2005 to Shenderova, et al. for all that is first disclosed at the time of filing of these applications; and Ser. No. 12/660,457 also claims priority benefit of U.S. Provisional Patent Applications No. 61/156,571 filed Mar. 2, 2009, 61/162,457 filed Mar. 23, 2009 and 61/233,950 filed Aug. 14, 2009. Each of the above applications is hereby incorporated by reference in its entirety.

STATEMENT REGARDING FEDERALLY SPONSORED RESEARCH OR DEVELOPMENT

Research relating to the technology described herein was sponsored in part by the Army Research Laboratory under Cooperative Agreement Number W911NF-04-2-0023; and in part by the Defense Advanced Research Projects Agency (DOD) Strategic Technology Office ARPA Order No. Ak27-00, issued by U.S. Army Aviation and Missile Research, Development, and Engineering Center under Grant No. W31P4Q-08-1-0003; and in part by SPAWARSYSCEN San Diego under Grant No. N66001-04-1-8933. A portion of the research relating to the present technology was not federally sponsored.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Nanodiamond particles and their aggregates may contain optically-active structures such as non-diamond carbon atoms, dopants (non-carbon atoms in the substitutional or interstitial position within diamond lattice), point defects, linear defects, planar defects, interstitial carbon atoms and/or complexes of the above which can possess photoluminescent properties. Examples of optical structures include, but are not limited to substitutional or interstitial nitrogen (N), nitrogen atom(s) complexes with vacancy(s) (V), substitutional or interstitial Si atom, Si atom(s) complexes with vacancy(s) and others.

Although nanodiamonds produced by detonation synthesis (detonation nanodiamond (DND)), often exhibit a small level of intrinsic photoluminescence (PL), for typical nanodiamond samples such PL is weak and not useful for many applications.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

Figure 1:
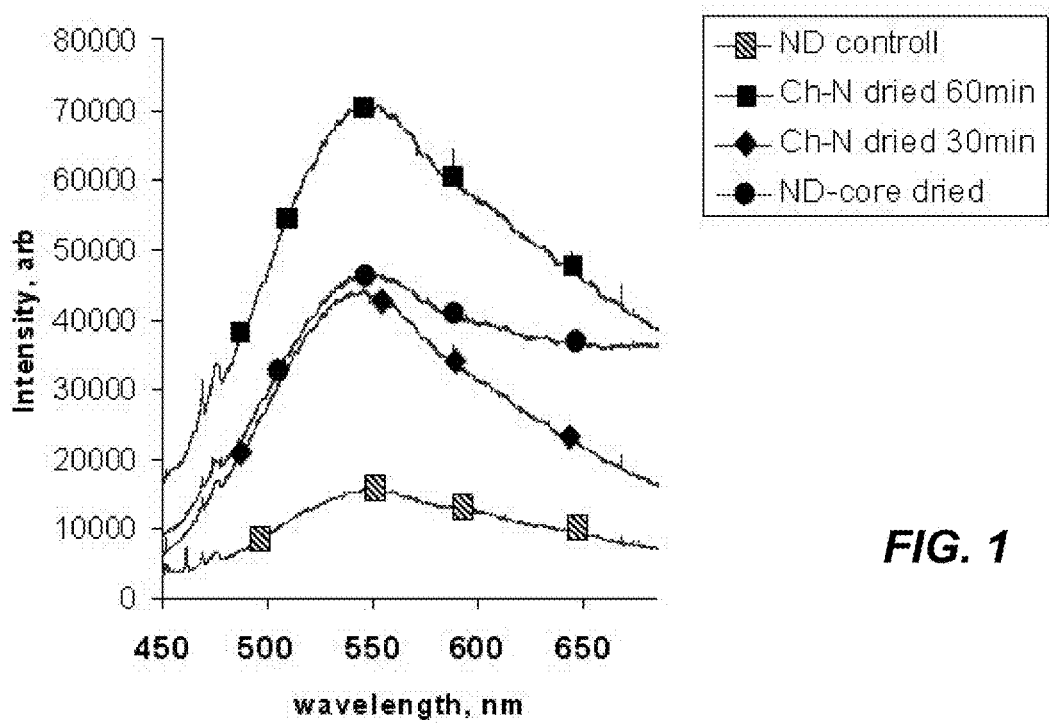
FIG. 1 depicts emission spectra for several DND samples immersed under mineral oil: without dehydration (ND control sample) and dehydrated before immersion under oil: ND-core (dehydrated for 40 minutes) and Ch-N (dehydrated by heating for 30 minutes and for 60 minutes); excitation wavelength is 442 nm.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment", "an example" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

For purposes of this document, the prefix "nano" as used, for example in "nanoparticle" or "nanodiamond" is intended to refer to particles having length in at least one dimension in the range of approximately 1-100 nanometers. However, in some particular cases, the length scale for achieving the novel properties and phenomena consistent with certain embodiments of the present invention may be less than 1 nanometer or be slightly larger than 100 nanometers. Agglomerates of such particles may be larger, for example several hundreds of nanometers. All sizes referred to herein are intended to mean the largest dimension in any direction.

As previously noted, nanodiamond particles and their aggregates may contain optically-active structures such as non-diamond carbon atoms, dopants (non-carbon atoms in the substitutional or interstitial position within diamond lattice), point defects, linear defects, planar defects, interstitial carbon atoms and/or complexes of the above which can possess photoluminescent properties. Examples of optical structures include, but are not limited to substitutional or interstitial nitrogen (N), nitrogen atom(s) complexes with vacancy(s) (V), substitutional or interstitial Si atom, Si atom(s) complexes with vacancy(s) and others.

Although nanodiamonds produced by detonation synthesis (detonation nanodiamond (DND)), have intrinsic photoluminescence (PL), for typical nanodiamond samples it is weak and not useful for many applications. It should also be noted that ND core is comprised of crystallographic lattice corresponding to a large extent to diamond cubic lattice. However, the diamond core may also include other diamond polytypes (such as for example, 2H or 6H polytypes).

In our previous U.S. patent application Ser. Nos. 11/991,090 and 11/990,948, we teach that possible mechanisms theorized for causing the absorption include absorption by the atoms with $sp^2$ bonding terminating a part of the particles surfaces; the surface groups involving other elements in addition to carbon; and absorption by internal defects in the bulk of diamond particles followed by photoluminescence and other phenomena. For example, there are several defect centers due to dopant atoms (N and other elements), self-interstitials, vacancies, complexes of the above, complexes of the charged defects, dislocations that cause absorption and photoluminescence, particularly at wavelengths shorter than 420 nm. That means that UV light is absorbed by these structural features and then is reemitted at a longer wavelength, primarily in the visible range of light for the case of photoluminescence. We also teach that the photoluminescence and other processes of conversion of absorbed UV radiation into emitted light in diamond particles are believed to be possibly due to defects that are present naturally as a result of material formation/processing or created by subsequent irradiation (for example, electron, ion or other types of irradiation) or obtained by subsequent annealing or are created by other means. We also teach that doping of ND to induce colored centers can be realized by several means including at the stage of detonation of the explosives used to produce the ND by the addition of materials to the explosives that induce color variations. Doping can be also induced by radiation and other means.

In our approaches as described below we teach how the intrinsic PL of detonation ND can be significantly enhanced. While examples below are given for detonation ND, teaching can be extended to other types of ND produced by other methods.

Often PL properties of the optically active structures depend on their charged state. For example, positively charged substitutional nitrogen-vacancy complexes do not demonstrate PL activity. Only neutral or negatively charged N-V complexes appear to posses PL properties.

Optically active point defects in bulk diamond, commonly called "color centers", can be charge acceptors and donors. Similar, surface defects and surface groups can be acceptors and donors. Most of the donors and acceptors in diamond have large ionization energies and therefore are predominantly neutral in uncompensated state at room temperature. A charge state of the centers is changed when donor-acceptor compensation takes place. "Deep" donors and acceptors are efficiently compensated when they are separated from each other by less than about 10 lattice spacing. For example, if color centers in the ND core with typical radius of 2 nm are donors, and at the ND surface there are acceptors, electrons efficiently transfer from donor to acceptor, so that the donor remains in a positively charged state and the acceptor is in a negatively charged state. Change of a charge state of PL active center can suppress PL activity of the center. On the contrary, if acceptors are substituted with donors on the ND surface, charge state and PL activity of the donor in the core is recovered. There can be different combinations between donors/acceptors residing in the core of ND particles or/and its surface. If the optical structures posses the 'right' charge state, then they exhibit PL. This depends on the proximity of other donors/acceptors which can result in the charge transfer and formation of the charge state unfavorable for PL and thus PL will be suppressed. In principle, donor/acceptor can be in the particle center and/or on the surface. If the ND particle is small, with radii equal or less than the efficient donor-acceptor compensation distance (defined as a maximal distance at which charge transfer may take place), all such centers will be influenced by the presence of surface groups playing a role of donor/acceptor. Thus, the ND surface should be specifically terminated to avoid the 'wrong' charge state of optical structures intended to exhibit PL. Alternatively, ND particle should be large enough that the charged state of the optical center residing in the ND core is not influenced by the proximity of the surface with surface groups causing charge transfer.

Hence, one approach for enhancing PL involves specific nanodiamond surface termination—terminating with non-diamond structures at the nanodiamond particle surface, including, but not limited to surface groups that are present as a result of synthesis, purification, and/or modification; species adsorbed from the environment, species forming solvation shells or solid-state shells, partial shells around the nanodiamond particle, as well as discrete functional conjugates and combinations thereof. Examples of nanodiamond termination include, but are not limited to hydrophilic or hydrophobic surface groups, an $sp^2$ carbon shell or partial shells, radicals, adsorbed water or gases (such as oxygen, $CO_2$, $N_2$, NO, $NO_2$), solvent molecules, polymer shells, silica shells, metal shells, oxide shells, silicon or germanium shells, organic or inorganic shells, ionic molecules such as nitronium ions that arise from the following reagents nitronium perchlorate ($NO_{+2}ClO_{-4}$), nitronium tetrafluoroborate ($NO_{+2}BF_{-4}$), nitronium hexafluorophosphate ($NO_{+2}PF_{-6}$), nitronium hexafluoroarsenate ($NO_{+2}AsF_{-6}$), and nitronium hexafluoroantimonate ($NO_{+2}SbF_{-6}$).

Another approach of PL enhancement includes high temperature annealing of DND in vacuum at temperatures that are much higher than those currently used for DND processing following synthesis. The temperature range of annealing in vacuum to enhance the photoluminescence is about 700-1400° C. for DND. Nanodiamond particles that have undergone the annealing conditions, which lead to the formation of a $sp^2$ shell on the surface of the ND particle followed by etching, exhibit both enhanced photoluminescence and infrared (IR) absorption due to the presence of some residual $sp^2$ bonded carbon. If the $sp^2$ layer covers the entire particle, the layer will absorb the luminescence.

Yet another approach includes irradiation of DND particles with high energy particles, electrons or ions, where DND particles are DND specifically functionalized (for example, with silanes), or DND annealed at high temperature, or DND incorporated into a polymer matrix or in organic or inorganic shell. Irradiation of these types of DND can be performed using an atmospheric pressure apparatus (as such developed at ITC) or a vacuum plasma system that creates a gas discharge.

Photoluminescent nanodiamond (ND) with bright emission based on nitrogen-vacancy (N-V) centers were produced before only from synthetic high-pressure high-temperature (HPHT) or natural diamonds with nitrogen (N) content up to about 300 ppm. These NDs have irregular shapes, sharp edges, are expensive, and the monocrystalline size distribution is large. NDs of static synthesis are intrinsically hydrophobic, which is not suitable for biological studies and requires additional surface treatments to make them hydrophilic. Thus, production of bright photoluminescent NDs (PL-ND) with a regular shape (spherical or polyhedral) and characteristic sizes below about 100 nm with a narrow size distribution remains an important but difficult to achieve goal.

Although nanodiamonds produced by detonation synthesis (detonation nanodiamond (DND)) from carbon-containing explosives, have a low level of intrinsic photoluminescence (PL), for typical DND samples it is too weak to be useful for many applications. However, DNDs are inexpensive to produce in large quantities, so it would be advantageous to produce enhanced PL properties in DNDs.

We have discovered that one of the possible problems for producing PL ND from detonation nanodiamonds is its high nitrogen (N) content that does not allow production of active optical centers and significantly enhanced PL, unlike that for HPHT or natural micro/nanodiamonds irradiated to form N-V centers by annealing of the irradiated sample. Another possible barrier is the high density of twins and other coherent and incoherent grain boundaries in DND. These defects sites may have high localized N concentrations. High N content is problematic because the N atoms at high concentration are prone to forming complexes that are non-optically active. High density of twins and other coherent and incoherent grain boundaries in DND is problematic because these defects can be places for nitrogen complexes formation as well as charged states in these defects may cause unfavorable charge transfer from the color centers and thus prevent photoluminescence.

The content of N in a typical DND core is approximately in the range of about 10,000-20,000 ppm (1-2 at. %). For the production of N-V centers, the N impurity in the diamond lattice should be in a substitutional state. When the N content is high, the N atoms may form complexes, which are optically non-active. In addition, at high concentrations, N atoms may suppress the optical activity of neighboring nitrogens. High N content in ND originates from the high N content in the precursor explosives itself (TNT (trinitrotoluene), RDX (hexane), benzotrioxofuraxan, triamino-trinitrobenzene and others) used for DND synthesis. For example, 50/50 mixture of TNT/RDX contains 21 atomic % of N.

Hence, we have determined that for the successful production of highly luminescent NDs of dynamic synthesis (by detonation), the nitrogen content in the final ND product should be regulated during the synthesis process by a different means. One aim is to reduce the N content in detonation ND by approximately at least one-to-two orders of magnitude as compared to typical detonation ND (10,000-20,000 ppm).

Adding graphite (or other carbon material) to explosives in the detonation synthesis method, has been found to allow the reduction of the overall N content in the precursor material, thus resulting in the reduced N content in the produced ND. N content in HPHT ND can be up to about 300 ppm. Using HPHT ND with such N content, it is possible to produce bright fluorescent ND based on formation of NV centers by irradiation and annealing. Thus the mass ratio between graphite (or other source of carbon) and explosive can be regulated accordingly in order to control the carbon-nitrogen (C/N) ratio. Graphite can be grinded/milled or otherwise processed to micron/submicron particle sizes and uniformly mixed with an explosive in a detonation charge to obtain uniform distribution of N over the sample and thus uniformly incorporate N to resulting ND product. Carbon fibers can also be used as precursor material for mixing with explosive(s). By such means, fluorescent diamond fibers/rods after phase conversion can be produced by further irradiation and annealing. Detonation ND produced by such means (from a mixture of graphite (or other carbon precursor)/explosive(s)), should be irradiated by highly energetic particles (electrons, protons, and others) as known in the art and possibly annealed to form nitrogen-vacancy complexes (NV, $N_2V$, etc) and other photoluminescent defects. Irradiation with highly energetic particles can be achieved for ND powders or suspensions in a liquid.

Graphite can be easily intercalated by various methods and with various elements. Using intercalated graphite (graphite where the guest molecules or atoms are located in between the graphite layers), which is mixed with explosive(s) as a precursor material for the detonation synthesis, can provide a means to embed intercalated elements into resulting ND product. These embedded elements (both metals and other elements) can provide new optical, magnetic, electrical and other properties to detonation ND. For example, intercalated graphite (for example, with Si-containing compounds) can be a useful precursor material for producing ND containing Si, which have photoluminescent centers that emit light in the NIR region. It is also possible to add SiC (silicon carbide) material or other Si-containing material to the charge. Every additive should preferably be uniformly mixed with explosives and other additives in the charge. It is also possible to produce ND containing magnetic impurities for a variety of applications (imaging by magnetic resonance, electromagnetic shielding and others). Other carbon precursor materials can be also intercalated with doping elements (intended for ND doping) and converted to diamond during the explosive detonation. Graphite or other carbon precursor material can be also doped with different elements (so that a dopant element is incorporated into the lattice of the graphite or other carbon precursor material). Then doped graphite can be mixed with explosive material and detonation of the mixture can be performed under negative oxygen balance conditions in a cooling media.

There is also possible a combination of explosives with lower N content than in the TNT/RDX mixture. For example, hexanitrostilbene (HNS, $C_{14}H_6N_6O_{12}$) contains less N per C atom. In the 50/50 mixture of TNT and HNS, there will be 15 at. % of N (less than in TNT/RDX mixture). Thus, variations in the type of explosives can in turn provide variation in the N content in the final ND product. Variations in the explosives can be used together with the addition of other carbon precursor materials. One goal (but not the only goal and not necessarily a requirement) is to produce ND materials with substitutional N contents lower than 1,000-2000 ppm.

It is also possible to use a laser for phase conversion of carbon (of the non-diamond carbon type) precursors to produce ND with controlled N content. Using onion-like carbon (OLC) as precursors with intercalated, controlled N content or containing a small DND core that always contains N (thus having low N content in the overall precursor structure) may also facilitate the production of ND that has reduced N content by irradiating the OLC using a pulsed laser. OLC containing ND cores can be obtained, for example, by vacuum annealing of ND at 1450K. In the literature, a precursor called micrographite that was dispersed in a liquid was used to produce nanodiamond by laser pulses. Here we suggest the use of OLC to facilitate the control of the resulting ND size and, in addition, N content. Intercalated graphite micron- and sub-micron particles and OLC intercalated with different elements (metals, Si and others) might be also useful in this approach for the production ND with incorporated elements that is important for the production of photoluminescent centers.

Hence, it is suggested that the production of PL ND may be obtained by using nanodiamonds (ND) that are produced by the detonation of a mixture of at least one type of high energy explosive and carbon precursor such as, for example, graphite, carbon black, carbon fibers, hydrocarbons, polyaromatic hydrocarbons and other carbon-containing precursors. ND synthesized by the above means would contain nitrogen in the amount that does not jeopardize the production of the active photoluminescent centers. PL ND can be obtained by irradiation of the detonation ND with high energetic particles followed by annealing, as known in the art. If the concentration of N is still high, annealing may not be necessary. The precursor graphite or other carbon materials can be also intercalated or doped with different elements. Graphite as a precursor contains very little N, generally only as an impurity. This should allow the production of ND with low N content that would have, preferably, ND containing substitutional N. Elements intercalated/doped to graphite can be also incorporated into the ND structure. Another approach is to use OLC or OLC-containing a diamond core as the precursor for the production of ND with a low N content obtained by the irradiation of the suspension of OLC with a laser. These NDs should then be further irradiated by highly energetic particles (electrons, protons or other ions), annealed, and then purified from non-diamond carbon for the production of bright fluorescent NDs.

The list below are methods and approaches for achieving enhanced PL of ND contemplated hereby:

Nanodiamond particles with surface termination groups that prevent electron transfer from optical centers residing in the core of the nanodiamond particle and thus resulting in enhanced photoluminescence of the above optical centers for the following terminations:

where surface termination is a dehydrated surface;

where surface termination is hydrogenated dehydrated surface;

where the ND surface is a surface depleted of oxygen-containing groups or molecular oxygen;

where nanodiamond particles are produced by detonation of explosives;

where nanodiamond particles have a size less than approximately 10 Bohr radius for an optical structure;

where surface termination is performed with siloxane groups having functionalities with an —O—Si backbone chemical structure;

where surface termination is performed with silane groups having functionalities with an —Si backbone chemical structure;

where surface termination is performed with a polydimethylsiloxane (PDMS) or other chemical derivative siloxane shell;

where surface termination is performed with a chlorosilane or other chemical derivative silane shell;

for ND suspensions, the dehydrated ND surface interfaces with a solvent, where the solvent is one of the following: oil, mineral oil, hydrophobic polymers, hydrophobic small molecules, hydrophobic liquids, chloroform, cyclopentanone or other anhydrous solvents;

nanodiamond particles interfacing a solvent or other environment preventing the formation of a positive charge on a nitrogen atom residing within the core of the nanodiamond particle or from complexes formed by a nitrogen atoms that contain internal defects and/or dopants resulting in enhanced photoluminescence;

nanodiamond particles interfacing a solvent, molecules, or other environment preventing the electron transfer from a nitrogen atom residing in the core of the nanodiamond particle or from complexes formed by a nitrogen atom that contains internal defects and/or dopants resulting in enhanced photoluminescence;

nanodiamond particles interfacing a solvent or polymer with high refractive index, close to the refractive index of diamond—this would reduce light scattering from nanodiamond surface and thus can enhance photoluminescence efficiency;

where ND surface interfaces with the environment formed by: vacuum, dehydrated air, dehydrated inert gas, drying agent (including but not limited to small molecules, adsobants, molecular sieves, silica gel, etc);

where ND surface interface(s) with the environment and the environment is a PDMS or other siloxane matrix;

where ND surface interface(s) with the environment and the environment is a PDMS or other polymer matrix;

nanodiamond particles produced by annealing in vacuum or inert gas in the temperature range 700° C. to 1400° C. and purified with an oxidizing agent, demonstrating enhanced photoluminescence in comparison with untreated particles;

nanodiamond particles synthesized by detonation of explosives and further produced by annealing in vacuum or inert gas in the temperature range 700° C. to 1400° C. and purified with oxidizing agent(s) with incomplete removal of $sp^2$ phase demonstrating enhanced photoluminescence in comparison with untreated particles;

nanodiamond particles synthesized by detonation of explosives and further produced by annealing in vacuum or inert gas in the temperature range 700° C. to 1400° C. and purified with oxidizing agent(s) with incomplete removal of $sp^2$ phase demonstrating enhanced photoluminescence in comparison with untreated particles and demonstrating enhanced VIS (visible) and IR (infrared) absorption;

nanodiamond-containing materials comprising nanodiamond particles and their aggregates containing optically-active structures located outside of the nanodiamond core and comprising non-diamond carbon structures covering at least part of nanodiamond surface; wherein non-diamond carbon structures comprise nanographite particles that are approximately one or several nanometers in size;

nanodiamond-containing material comprising nanodiamond particles containing optically-active structures, whereby the optically-active structures comprise imperfections in the diamond crystallographic lattice combined with the structures located outside of the nanodiamond core and the observed enhancement of photoluminescence is a result of this combination;

nanodiamond particles synthesized from explosives with lower N content than in TNT/RDX (trinitrotoluene/hexane) mixture demonstrating enhanced photoluminescence as compared to particles produced from TNT/RDX mixture;

nanodiamonds with dopants other than N that are introduced during the synthesis (for example Si), (introduced by the inclusion of precursors to the explosives or to the cooling media (for example, $SiH_4$));

nanodiamond particles in the PDMS or other polymer matrix irradiated with ions protons, high energy beams or electrons demonstrating enhanced photoluminescence;

nanodiamond powder with silicon surface groups irradiated with ions, protons, high energy beams or electrons demonstrating enhanced photoluminescence;

nanodiamond powder with modified surface groups irradiated with ions, protons, high energy beams or electrons demonstrating enhanced photoluminescence;

nanodiamond powder annealed at high temperature (700-1400° C.) and subsequently purified from $sp^2$ carbon, irradiated with ions, protons, electrons or high energy beams demonstrating enhanced photoluminescence;

detonation soot irradiated with ions, protons, high energy beams or electrons and purified with oxidizing agent (mixture of nitric\sulfuric acids) with incomplete removal of $sp^2$ phase demonstrating enhanced photoluminescence in comparison with particles completely purified from $sp^2$ phase;

nanodiamond powder purified from $sp^2$ carbon, irradiated with ions, electrons, or high energy beams demonstrating enhanced photoluminescence; and combinations thereof.

Regarding further details on Si-containing compounds, they are as follows. The nanodiamond-containing material may contain optically active structures located on the surface of nanodiamond particles and comprise structures associated with silicon atoms and/or silicon containing functional groups. Silicon atom containing organic compounds include, but are not limited to, aminopropyltriethoxysilane, tricosane silane, phenyl dimethyl silane whereby the silicon atom contains a silicon ester, or an oxygen bridge Si-OR, whereby the R group is composed of an organic moiety; these compounds are called alkoxysilanes. Also the silicon atom containing silica-inorganic compounds include, but are not limited to, silica made of $SiO_2$, or any other combination of SiOR, where R is an inorganic compound, including but not limited to silicon, zirconium, aluminum, and/or magnesium. Silicon atom containing compounds may include, but are not limited to, silicon atom in combination with an organic or inorganic compound that contains a silicon-carbon bond or SiR, called silazanes or organosilanes. Another example is silicon atom containing compounds of the formula $R_3SiO$— with at least one oxygen atom are called siloxanes. The R group may be of oxygen, thus $R_3SiO$ that has four bridging atoms on silicon may be one of the following derivatives, for example: $(CH_3)_3SiO$—; $(CH_3)_2Si(O)_2$—; $(CH_3)Si(O)_3$—; $Si(O)_4$—, whereby the oxygen atoms are coordinating to other atoms. The R group may be an organic group of any form containing carbon. If the unit is repeating, then it is called a polysiloxane. The photoluminescence intensity of the said complexes can be further enhanced by high energy irradiation, including but not limited to electron, proton, or other ion beam irradiation of the Si/ND complex.

In the series of experiments below we demonstrate that nanodiamond (ND) particles and their aggregates may contain optically-active structures that are formed by non-diamond carbon atoms (presumably in amorphous, graphitic or other states) and show that the enhanced photoluminescence is caused by the presence of some type of residual $sp^2$ bonded carbon which, in addition, can be functionalized. We also teach how to obtain these PL nanocarbon-decorated nanodiamonds inexpensively.

In this series of experiments detonation soot was obtained by the detonation of a mixture of TNT/RDX in ice cooling media (wet synthesis) or obtained by a dry synthesis (dry cooling media). Detonation soot was treated in a mixture of $H_2SO_4/HNO_3$. The sample was heated at temperature above 90° C. for different time intervals (from 10 minutes to 2 days). After placing the collected reaction mixtures on a bench under UV light, all the reaction mixtures demonstrated surprisingly strong photoluminescence of different colors depending on the conditions of treatment and the type of soot treated. Then, samples were neutralized with NaOH and carefully washed with DI water multiple times until the DND had acquired a high negative zeta potential (at least −35 mV) and at least part of NDs remained suspended in DI water. We also used a 3500 molecular weight cut-off membrane for the separation of the ND and nanocarbon particles that were not attached to the ND. The collected nanocarbon particles that went through the membrane had sizes less than 1 nm, as measured by photon correlation spectroscopy.

Carefully washed ND (for pellets colored grey and a colloidally stable supernatant colored amber) demonstrated a surprisingly strong PL when observed with an inverted fluorescent microscope. While the typical DND can be seen under green light excitation at approximately 1500 ms exposure time (at ×60 magnification), the bright PL samples of the reaction product were seen at only 100-200 ms exposure time. The PL spectra demonstrated a factor of 20 times enhancement of red luminescence in these samples as compared to typical DND from detonation synthesis. The PL of the particles did not bleach under sustained photoirradiation. A sample of detonation soot boiled in the mixture of nitric and sulfuric acids for 2 hrs, demonstrated strong red luminescence under UV light 2 years after the treatment; this demonstrates that these structures are chemically and photonically robust.

While not intending to be bound by theory (here or in any other part of the present document), it is speculated that during the treatment of the detonation soot, the mixture of nitric and sulfuric acids produces hybrid structures: ND decorated with nanocarbon (non-diamond phase) particles. This nanocarbon species may contain amorphous carbon, polyaromatic amorphous carbon, mixed $sp^2$-$sp^3$ carbon phases, diamond-like carbon, resemble graphite structures or form graphene ribbons or some other carbon-based structures. It is not excluded that some molecular species contributing to PL can be formed too. Our conditions of treatment included refluxing in a mixture of sulfuric/nitric acids chosen to avoid complete etching of non-diamond carbon structures. There are methods of removing oxidized and non-diamond forms of carbon by treatment with a mixture of concentrated nitric and sulfuric acids (or the acids with addition of sulfur anhydride) at temperatures exceeding 250 degrees Celsius for several hours (see, for example, an example from U.S. Pat. No. 5,861,349). The conditions of treatment described in U.S. Pat. No. 5,861,349 correspond to removal of non-diamond carbon from DND surface, which is considered standard practice in producing high purity nanodiamonds. However, in our method the process of refluxing at lower temperatures with careful control of reaction time allows us to control the amount of non-diamond carbon left on DND surface, resulting in appearance of PL properties. Conditions of treatment should preferably be chosen to allow control over the formation of PL non-diamond carbon structures on the DND surface.

By oxidizing candle soot and other types of all-$sp^2$ carbon soot such as, for example, arc discharge soot containing carbon nanotubes (X. Xu et al. J. AM. CHEM. SOC. 2004, 126, 12736-12737) it is possible to produce PL carbon species. Specifically, by refluxing in the mixture of $HNO_3$ and DI water of candle soot or arc discharge soot for many hours, luminescent carbon-containing nanoparticles can be obtained after additional manipulation. Other ways of forming PL carbon species include electrochemical treatment, treatments with microwave, perchloric acid, tetrafluoroborate ionic liquids. In the case of arc discharge soot, after electrophoretic separation, fluorescent carbon particles of 1-2 nm in diameter or short tubular carbon species can be obtained (X. Xu et al. J. AM. CHEM. SOC. 2004, 126, 12736-12737). Single-wall nanotubes (SWNT) are also present in arc-discharge soot but they do not become fluorescent during refluxing in nitric acid after separation from the carbon nanoparticles. In another work by Sun et al. (J. AM. CHEM. SOC. 2006, 128, 7756-7757), several nanometer-sized nanocarbon particles were produced by laser ablation of a carbon target and refluxed for 12 hrs in aqueous nitric acid solution (up to 2.6 M). But they were not photoluminescent until covered by poly-(ethylene glycol) (PEG) functional groups. These examples demonstrate how unique are the phenomena observed in our experiments. Highly luminescent structures are produced within minutes, whereby the PL carbon nanoparticles may be permanently attached to the ND; at the same time, part of PL carbon nanoparticles not attached to ND during detonation soot treatment can be isolated as free structures in the supernatant by centrifugation. These bright PL ND-nanocarbon structures as well as free standing PL nanocarbons do not require any additional surface passivation with other molecules (like PEG). However, it is noted that materials produced by the methods taught herein may be passivated to increase the photoluminescence effects.

Carbon dot structures have been reported in the literature and are particles of nanographite from approximately 6 nm to approximately one nanometer in size. However, it was highly surprising that after short heat treatment of detonation soot containing NDs as obtained by detonation of carbon-containing explosives in the mixture of $H_2SO_4/HNO_3$, the particles with bright PL were obtained with large diamond agglomerate sizes (tens of nanometers and hundreds of nanometers). Possibly the DND surface has the effect of 'mirrors' that reflects the light emitted by PL nanocarbon structures attached to ND, so that large luminescent structures can be obtained. It can be also hypothesized, that the carbon nanostructures themselves serve as passivating coatings that allow the nanodiamond core defect states to become stabilized, similar to silicon functionalized ND and dehydrated ND. In one example, we produced ND-PL nanocarbon fractions with an average particle size of 50 nm, which may be further fractionated to smaller particle sizes that are useful for biomedical applications. Initial soot can be milled (by dry or wet milling) before treatment in the mixture of acids and this would also facilitate the production of smaller luminescent ND-carbon dots structures. Bright PL ND-nanocarbon structures presumably have carboxylic acids groups on their surface based on the high negative zeta potentials of the structures after careful washing. These groups are very useful for further functionalization of the ND surface using standard wet chemistry synthetic methods.

Nitrogen-containing groups can be also formed since nitric acid is used in the reaction, as well as a variety of nitrogen oxides, which are clearly present from the samples that are red/yellow colored for the unwashed supernatant as seen in white light. Nitronium ions are also expected as terminating surface species. It is also possible that different surface groups are formed depending on the conditions of the reaction and degree of oxidation (etching). Our procedures use ranges of time from minutes to at least 2 hours of treatment to achieve these highly PL particles. Depending on the limitations on the content of non-diamond carbon presence in the sample and level of PL intensity, different duration time and temperature of treatment can be chosen for different applications. Since tons of detonation soot are currently available, this method provides prospects for inexpensive production of PL nanocarbon and PL ND-nanocarbon particles.

It can be assumed that during detonation of explosives, the nanodiamond lattice forms monolithic structures with surrounding graphitic regions (for example (111) diamond planes can be commensurate with graphite basal plains). During controlled etching of non-diamond carbon (as in our procedure), it is possible that PL carbon particles are nanographitic islands on ND surface that remain from incomplete etching of an $sp^2$ 'mantle' surrounding the detonation ND particle.

We also discovered that this high temperature treatment using the mixture of nitric/sulfuric acids of many different types of carbon structures (graphite, onion like carbon, Ni encapsulated into carbon coating, SWNT, carbon fibers) produce bright PL supernatant solutions. While the PL species may be collected and used independently, it is also possible to produce hybrid structures of these PL species with nanodiamonds that will also possess PL properties. As will be described in the examples below, it is possible to first produce PL nanocarbon separately from, for example, high temperature sulfuric/nitric acid treatment of micrographite. The collection of this supernatant that contains the PL nanocarbons/carbon-containing species may then be added to nanodiamond particles for continued high temperature treatment. In this treatment, nanocarbon particles strongly attach or adsorb to NDs. We also noticed that while PL nanocarbons, being negatively charged, are strongly adsorbed to ND with positive zeta potential, after mixing of PL nanocarbons with negatively charged ND and washing, ND did not acquire photoluminescence (PL nanocarbons were not attached). A wide variety of approaches may be used to produce PL carbon-based species as suggested from this work. We also demonstrated in U.S. patent application Ser. No. 12/592,354 filed Nov. 24, 2009 (which is hereby incorporated by reference) that small sized DND particles can function as a surfactant to CNT (show affinity to CNT). Thus, there are ways to impart PL to other nanostructures through chemical, ionic or van der Waals bonding of PL ND-nanocarbons.

It is also possible, that the nanographite species attached to ND surface can reduce charge transfer from the interior color centers of ND and thus allow for the activation of PL.

We also noticed that changing the pH of the nanocarbon-nanodiamond suspension can change the PL color of the discovered materials. The size selection of PL nanocarbon particles as well as ND-nanocarbon structures is also one of the ways to control emission color. We observed samples emitting from blue, violet, green, yellow, orange to red colors when placed under a UV lamp. These structures emit in the NIR region also (based on PL spectra).

The high luminescence and IR absorbing characteristics of DND can be used in a wide variety of applications including but are not limited to cellular tracers, bio-labels, bio-tags, bio-sensors, chemical-sensors etc. They can be used in labels and tags, such as bar codes, which are undetectable except under certain conditions, such as excitation. They can be used as tags where the temperature may rise substantially, such as tracers in gun powder or explosives. They may be used as markers in samples that undergo heating or annealing such as sterilization in an autoclave. They can be also valuable research tools in development of DND-based nanocomposites since they will allow visualization of DND distribution within the matrix and facilitate the development of the nanocomposite processing. Those skilled in the art will recognize many other practical applications upon consideration of the present teachings.

These fluorescent NDs can be used as imaging agents in cell studies as well as labels for study of the biodistribution of ND and ND conjugated with biomolecules in the organs and tissue. It is possible to dissolve tissue by strong oxidizers (acids), collect ND and measure its photoluminescence from a unit mass of the tissue for biodistribution studies. Similar, their photoluminescence from unit area of the separated and sliced organ can be detected from a sacrificed animal. It can be useful also in vivo experiments for imaging of ND and/or with attached diagnostic/therapeutics agents. It can be also useful in biodetection. Through binding bio-moieties, cells, viruses, followed by burning of the bio-mass and measuring PL signal from the collected remaining ND, it is possible to quantify the amount of bio-moieties bound to ND and collected by ND. Photoluminescent ND can be also used in seeding over surfaces as well as in different composites for imaging and tagging/marking. Those skilled in the art will recognize many other practical applications upon consideration of the present teachings.

Examples below demonstrate our success in production of highly luminescent DND.

Example 1

PL Enhancement in Vacuum

DND powder (DND purified from soot using a mixture of sulfuric acid and chromic anhydride) was placed to a quartz cuvette and treated for 20 min at 150° C. at vacuum 20 torr demonstrated enhanced photoluminescence, as was observed in the fluorescent microscope of the cuvette containing DND.

In another set of experiments, tablets of DND mixed with KBr and pressed were placed in an IR vacuum cell and heated at 200° C. under vacuum ($1 \times 10^{-2}$ torr.) for 3 hours to remove traces of adsorbed water. Following this procedure, FTIR spectra were recorded without exposing the samples to air to avoid the influence of atmospheric water on the spectra. DND samples with different surface chemistry (hydroxylated, hydrogenated, etc.) exhibited strong peaks in spectra taken in vacuum around 1135 cm$^{-1}$ which were not characteristics of spectra taken in air. These peaks are believed to be attributed to neutral substitutional nitrogen, which is important for existence of PL in DND. When water is adsorbed (spectra taken in air), it is possible that nitrogen centers are positively charged, and such centers do not have strong peaks around 1135 cm$^{-1}$ and are not seen in the spectra.

Example 2

PL Enhancement: ND Dehydrated by Heat Treatment and Preserved Under Oil

Several DND samples were dehydrated on a hot plate at 150° C. for 30-60 minutes and covered with mineral oil (while on a hot plate). Sample I6 control is a control sample of DND not heated on a hot plate for dehydration. I6 DND was purified from soot using a mixture of sulfuric acid and chromic anhydride and then additionally purified using $H_2O_2$/NaOH treatment and ion exchange treatment. As-is I6 control powder was covered with oil. Samples Ch-N were obtained by additional purification of I6 by boiling in nitric acid, washing and drying. Then samples were heated on a hot plate for 30 min and 60 minutes and covered with mineral oil. Sample ND core was obtained by heating I6 at 1400K and purifying with a mixture of nitric/sulfuric acids to remove non-diamond carbon. Then sample ND core was washed and dried on a hot plate to remove adsorbed water and covered with oil for PL measurements. PL spectra illustrated in FIG. 1 demonstrated PL enhancement of a factor of several times as compared to not-dehydrated control sample under oil. The refractive index of the oil is relatively high (1.46); this could help to reduce losses for light scattering.

In this and following below experiments emission intensity was measured from a thick (~500 mikron) DND pellet dispersed over Si substrate. PL intensity was measured with standard equipment for measurement of PL spectra. In our case, photoluminescence spectra were recorded at room temperature using a LABRAM HR spectrometer with an Ar+ laser for excitation. The laser radiation of 1 mW power at 488 nm wavelength was focused in a spot of 2 μm in diameter on the surface of the DND samples. We also used Raman and PL Spectroscopy device Horiba Jobin Yvon LabRam ARAMIS to take PL spectra of the samples. To assure in consistency of results, spectra were typically taken at several points.

Example 3

PL Enhancement: Functionalized/Modified ND

DND functionalization was performed with silicone-containing groups aminopropyltriethoxysilane or APES ($Si(OC_2H_5)_3(CH_2)_3NH_2$, diphenyl dichlorosilane ($SiCl_2(C_6H_5)_2$) and 10-(carboxymethoxy)decyldimethylchlorosilane ($Si(CH_3)_2C_{10}COOCH_3$), all purchased from Gelest Inc. denoted as ND-APES, ND-Ph and ND-silyl, respectively. The condensation reaction of DND functionalized with hydroxy groups was performed in a solution of toluene. The ND-OH was suspended in dry toluene and the silane functional group was added drop-wise into the solution. After addition, the DND was washed with toluene by pelleting to remove nonfunctionalized silane.

Figure 2:
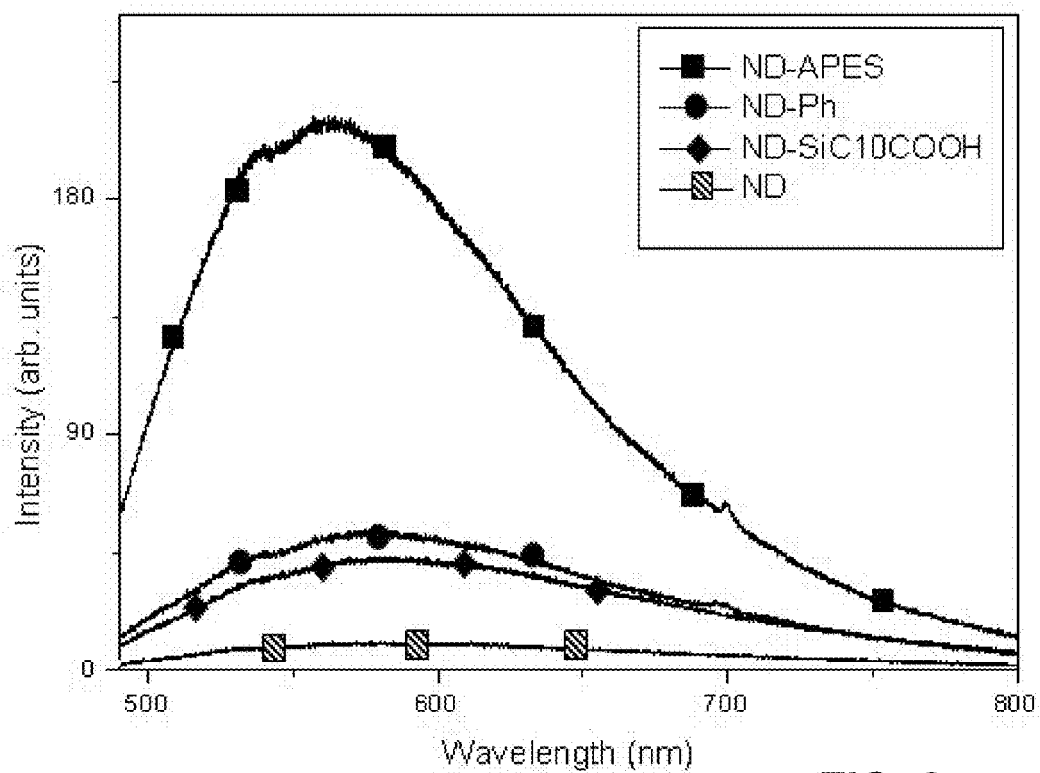
FIG. 2 depicts the PL spectra measured in 10 min after beginning laser irradiation for the pristine DND powder (control), and 3 types of functionalized DNDs: ND-APES, ND-Ph, ND-SiC10 (denoted as ND-SiC10COOH); excitation wavelength is 488 nm.

We observed that the DND-siloxanes, including DND-APES, DND-phenyl dimethyl, DND-tricosan siloxane, DND-silyl exhibited up to about ten times the PL emission intensity as compared to typical DND (initial DND used for the functionalization) as it is demonstrated in FIG. 2.

Hydrogenated DND exhibited PL enhancement that was about three times greater than PL for the initial DND taken for the hydrogenation in a gas flow reaction.

ND-APES structure demonstrated stable photoluminescence that did not decrease with time and was about ten times higher in PL intensity as compared to the conventional DND control sample.

Example 4

PL Enhancement: ND Produced from Explosives with Lower Total N Content than in TNT/RDX (Trinitrotoluene/Hexane) Mixture (40/60)

ND produced from the mixture TNT/HNS (hexanitrostilbene) demonstrated about two-three times enhancement of PL as compared to ND produced from the mixture TNT/RDX. According to electron energy loss spectroscopy (EELS), the nitrogen content in DND produced from TNT\HNS mixture is about 3 times lower as compared to DND produced from the TNT/RDX mixture. This example shows that by varying the composition of the precursor material for the synthesis of detonation ND, it is possible to control the N content in the produced ND and, therefore, control its PL properties.

Example 5

PL Enhancement: Thermal Annealing

We demonstrated that high temperature annealing in vacuum of DND results in enhanced photoluminescence. First, DND was annealed in vacuum ($10^{-4}$ Torr) at 1400K for 1 hour. Then, the outer $sp^2$ shell that formed was removed using strong acid, exposing the DND core. Analysis of the resulting sample using an inverted fluorescence microscope for observation with UV and green excitation light showed more than three times enhancement of the photoluminescence. The average particle size is expected to be smaller than the original average primary particle size due to the conversion and removal of the outer shell.

These results provide evidence that thermal annealing in vacuum of detonation ND is a possible method to create enhanced photoluminescence by the formation of different types of nitrogen centers and vacancies arising from the intrinsic nitrogen and vacancy defects present in the as-produced DND. To further enhance the PL, the samples can be functionalized or irradiated.

Example 6

PL Enhancement: Nanodiamond Size Selection

In our approach we teach how the intrinsic photoluminescence (PL) of nanodiamonds (ND) produced by dynamic synthesis can be significantly enhanced using size-selection of nanodiamond crystals and induced nitrogen-related optical centers. While the examples below are given for detonation ND, the teaching can be extended to other types of ND produced by other methods.

In the experiment described below, it was found that if the DND primary particle sizes (crystal sizes) exceed approximately 10-15 nm, N-V centers can be formed following irradiation with highly energetic particles followed by annealing. This tentatively can be attributed to the existence of regions with fewer defect structures in larger diamond particles, where the nitrogen may be embedded in the single substitutional state during synthesis. We demonstrated that it is possible to select DND with primary particle sizes exceeding approximately 10-15 nm, irradiate them with highly energetic particles (we used electrons), anneal them and obtain N-related defects with high intrinsic PL. These findings demonstrate that through manipulation of size/nitrogen content in DND there are DND sizes above which in combination with the N content production of PL DND is possible.

It can be also hypothesized that in larger crystals, a larger size may prevent charge transfer from internal color centers to surface acceptors. Here we would like to emphasize that under crystal we mean a diamond particle containing subgrains with high cohesive energy, such as twin grain boundaries or other coherent boundaries. It is not possible to further break such particle by bead milling. Under crystal size we mean a minimal diameter of the imaginary sphere that enclose a particle completely.

Figure 3:
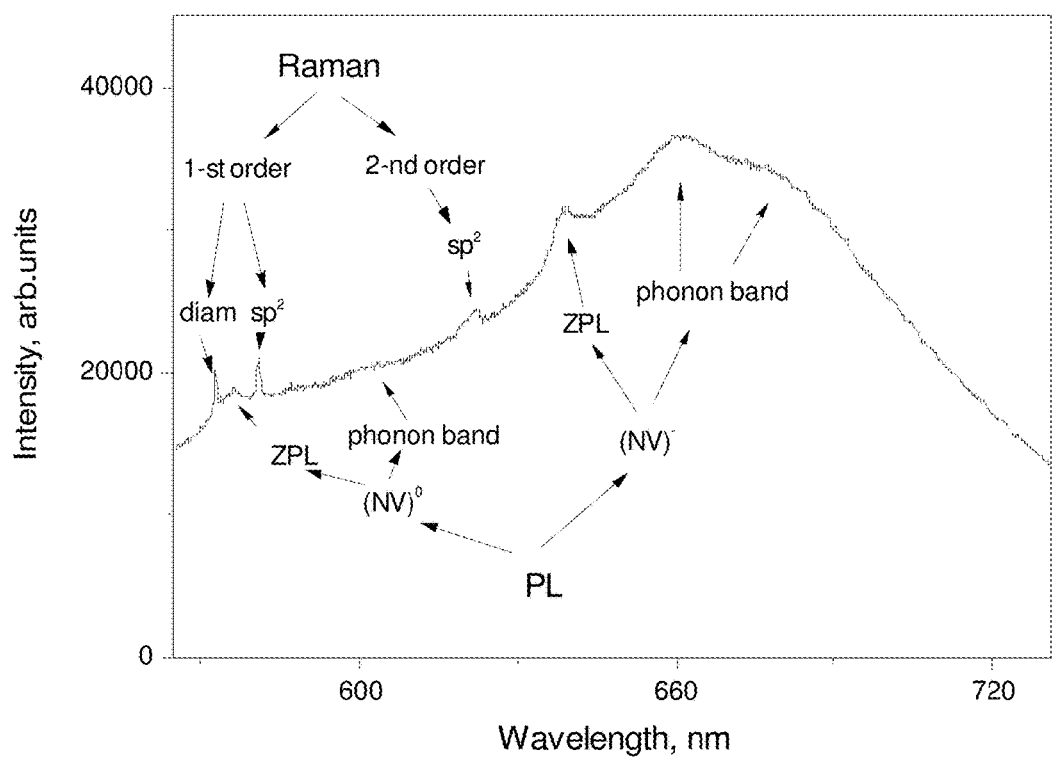
FIG. 3 depicts the PL spectra of a bright spot of DND indicating the presence of NV defects, where the diamond line in Raman spectra is positioned at 1332 cm$^{-1}$.

The nanodiamond used in this experiment was purchased from New Technologies, Chelyabinsk, Russia. The nanodiamond particles were synthesized by the detonation of a mixture of trinitrotoluene (TNT) and hexogen (40/60) in an ice cooling medium, followed by a soot purification process using a mixture of sulfuric acid with chromic anhydride, washing with DI water and drying. Then the sample was additionally purified to remove metal impurities by boiling in a $NaOH/H_2O_2$ mixture followed by washing in DI water, treating with ion-exchange resins and drying. The sample was called I6. Subsequently the powder was dispersed in the solvent dimethylsufoxide (DMSO) and fractioned by centrifugation to a slurry with average aggregate size of 60 nm. DND was dispersed over a silicon substrate by immersing the substrate in the slurry of DND followed by treatment for 10 minutes in an ultrasonic bath. Then the substrate was rinsed with methanol and dried. Then the substrate with dispersed DND was irradiated with 2 MeV electrons at a dose $5 \times 10^{18}$ $cm^{-2}$ and annealed in vacuum at 700° C. for 1 hr. Using a Raman/PL spectroscopy system in image mode in combination with a cut-off filter (passing light with wavelength >630 nm) an image of the emission distribution from the DND film on the substrate surface illuminated with a 532 nm laser was obtained. Bright PL spots with stable emission were clearly visible in the image. A typical Raman-PL spectrum measured in one of the bright spots is shown in FIG. 3. Two lines at 575 nm and 638 nm, related to the zero-phonon electron transitions in neutral nitrogen-vacancy) ($NV^O$) and negatively charged nitrogen-vacancy ($NV^-$) defects are clearly seen in the spectrum. The diamond line is positioned at 1332 $cm^{-1}$ indicating the relationship of the emitting spots with diamond crystallites larger than approximately 10-20 nm. It is possible that DND with smaller sizes also acquired photoluminescence, although not as bright as the PL from the spot shown in FIG. 3 from larger DND crystallites. Raman spectra were also taken from HPHT synthetic diamond powder with average crystallite size 10 nm (as measured by light scattering technique). The diamond line was positioned at 1332 $cm^{-1}$ indicating that low-defected diamond crystals with average size 10 nm can possess a 1332 $cm^{-1}$ diamond peak.

The observed PL was stable over time. Thus after the noise signal from smaller particles not containing N-V centers was eliminated by dispersing DND over a substrate and studying PL properties of a small amount of bright DND particles which appeared to be particles with crystallite sizes larger than average (4-6 nm) DND, the N-V signal was easily detected.

Example 7

ND Crystal Size Control and Selection; N Control During Synthesis

Figure 4:
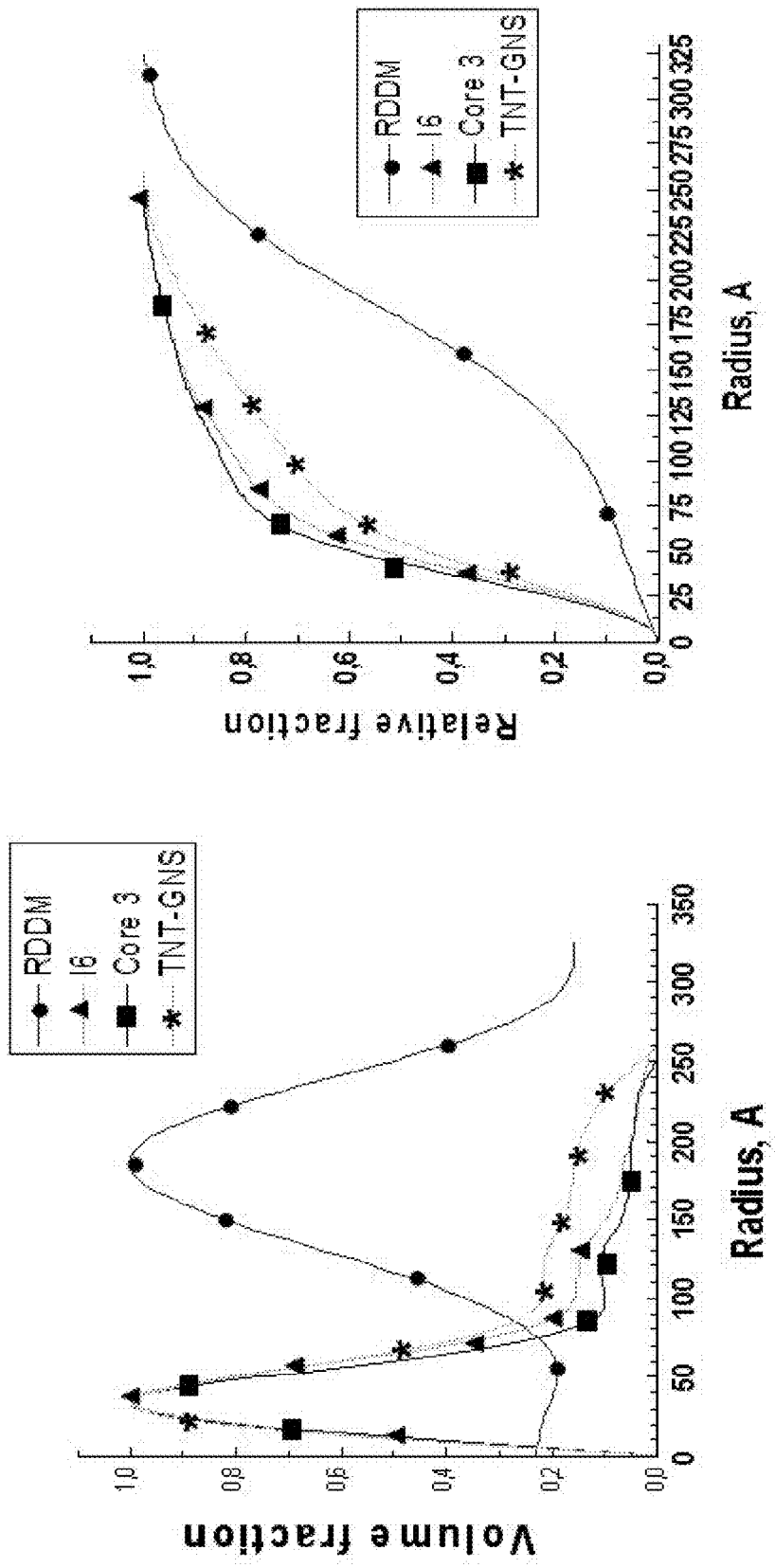
FIG. 4 depicts volume size distribution of nanodiamond particles based on SAXS technique (left) with the relative fraction of nanodiamonds with a size below a given size (right) (so called undersize curve).

In order to define which fraction of DND that can be used for production of bright photoluminescent DND, a size distribution of nanodiamond crystallites in the studied DND powder was analyzed by the small angle x-ray scattering (SAXS) technique. The samples used in this experiment were DND I6 from example 2, as well as DND I6 annealed in vacuum and purified (Core 3), a sample produced from trinitrotoluene/hexanitrostilbene explosives (called TNT-GNS) and a sample produced from graphite-explosives mixture (RDDM). The dependence of the SAXS intensity on the characteristic sizes of the crystallites is shown in FIG. 4. The maximal intensity of SAXS corresponds to the grains of approximately 6 nm in diameter, meaning that the fraction of 6 nm crystallites is dominant in the DND powder. The tail in the size distribution spreading beyond approximately 15 nm reveals that the conditions of an explosive synthesis are not equal for all particles produced and a small volume fraction of the DND differs essentially in size from the main product.

DND produced by different means (I6, Core 3, TNT-GNS) have different fractions of primary particles with sizes exceeding approximately 10-15 nm. For example, approximately less than 45% of DND with primary particle size larger than 10 nm can be found in the original powders of nanodiamonds produced from explosives (FIG. 4, right). Approximately less than 25% of DND with primary particle size larger than 20 nm can be found in the original powders of nanodiamonds produced from explosives (FIG. 4, right). For the RDDM sample produced from a graphite-explosive mixture the average primary particle size (crystallite size) is around 35-40 nm. The RDDM sample also contains much less N incorporated to the grains as it follows from EELS spectra.

For successful production of highly luminescent ND by dynamic synthesis (by detonation), the nitrogen content in the final ND product should be controlled during the synthesis process by different means. In addition, primary particle sizes also should be regulated during synthesis or through the use of a post synthesis processing—for example, fractionation after full deagglomeration or annealing\oxidation eliminating DND with smallest sizes.

Example 8

Methods of Size Selection

In this example, typical DND was bead milled and fractionated to narrow size fractions. Then Raman spectra were taken for the smallest fraction, 5 nm ND and a fraction, depleted from the small 5 nm primary particle size (with average particle sizes approximately 20-15 nm as measured by the dynamic light scattering technique). The Raman peak for the smallest fraction (fraction 1) was 1325 $cm^{-1}$ and for the fraction depleted from the primary 5 nm particles (fraction 2)–1329 $cm^{-1}$. The larger Raman shift for the fraction 2 of the DND indicates that this fraction contains more particles with larger crystallite sizes. Thus, DND can be fractionated in a way that DND with primary particles with sizes larger than approximately 10-20 nm can be extracted from de-agglomerated ND material.

Known methods of fractionation can be used such as, for example, ultracentrifugation, tangential flow filtration, diafiltration and other techniques. Also, a known in the art method of increasing the average ND crystallite size is the elimination of smaller particles by oxidation or etching. ND crystallite size can be also increased by sintering of NDs under HPHT or compaction by a detonation wave as described in the literature.

Example 9

PL Enhancement: High Energy Irradiation

In this experiment we followed the procedure described in the U.S. Patent Publication 20080118966 by Chang, et al. on irradiation of nanodiamond with high energy protons and annealing. We learned in this experiment that detonation ND does not acquire so bright luminescent properties under irradiation with protons, as it was demonstrated to take place by Chang et al. for HPHT nanodiamond of static synthesis.

Figure 5:
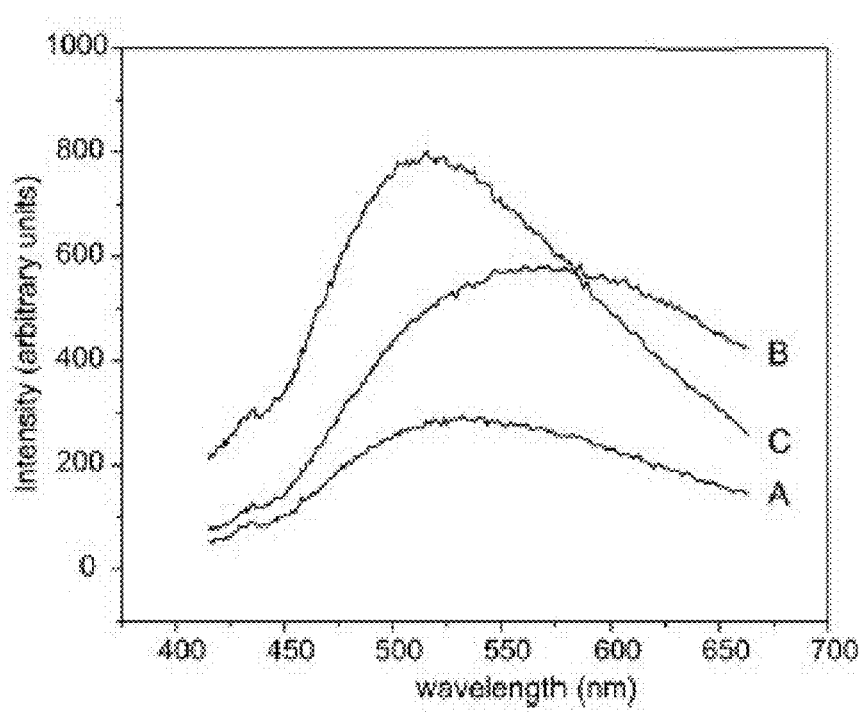
FIG. 5 depicts the emission spectra for the pristine DND powder (A), powder irradiated at a dose $4.8\times10^{15}$ cm$^{-2}$ (B) and irradiated and annealed at 600° C. powder (C); excitation wavelength is 406 nm.

DND I6 (as described in example 2) used in this experiment was produced from a mixture of TNT/RDX and further purified from $sp^2$ carbon and metals and fractionated down to 120 nm aggregate size. Average coherent scattering region size as obtained from x-ray diffraction (XRD) is 4 nm. Emission spectra for the pure ND powder samples recorded with 406.7 nm excitation using a Dilor Raman spectrometer are shown in FIG. 5. Spectra for the untreated (sample A), proton-irradiated (fluence $4.8 \times 10^{15}$ protons $cm^{-2}$) (sample B) and irradiated followed by annealing the ND powder (sample C) are provided. The emission of pure untreated ND powder shows a broad band centered at 530 nm, typical for detonation ND. After proton irradiation the band maxima position is red shifted to 565 nm. The intensity increased and the band becomes broader. After annealing at 600° C. in an $N_2$ atmosphere, the band maxima position is blue shifted to 515 nm. The distribution becomes narrower, indicating that some defects were annealed, especially defects contributing to red emission (under excitation at 406 nm). As can be seen, the increase in PL intensity is less than 4 times. Thus, the effect of inducing PL by irradiation of typical DND with protons is much less effective than for HPHT. It should be noted that the PL intensity of the irradiated ND powder at a dose $3.2 \times 10^{16}$ protons $cm^{-2}$ was below the sensitivity threshold of the LS-50B Luminescence Spectrometer from Perkin-Elmer, indicating that the PL of irradiated pure ND powder is lower than the PL intensities for the ND-PDMS composite and pure PDMS, irradiated at the same fluence as ND powder.

Thus in order to make photoluminescent ND produced by detonation of explosives, different strategies are needed as compared to HPHT ND (ND of static synthesis) for which PL intensity can be efficiently enhanced through irradiation with high energetic particles and annealing.

Example 10

PL Enhancement: Silicon Functionalized Nanodiamonds

In this work, DND functionalization was performed with silicone-containing groups aminopropyltriethoxysilane or APES ($Si(OC_2H_5)_3(CH_2)_3NH_2$, diphenyl dichlorosilane ($SiCl_2(C_6H_5)_2$) and 10-(carboxymethoxy) decyldimethylchlorosilane ($Si(CH_3)_2C_{10}COOCH_3$) denoted as ND-APES, ND-Ph and ND-silyl, respectively similar to example 3. Then, these samples were proton-irradiated (fluence $4.8 \times 10^{15}$ protons $cm^{-2}$).

Figure 6:
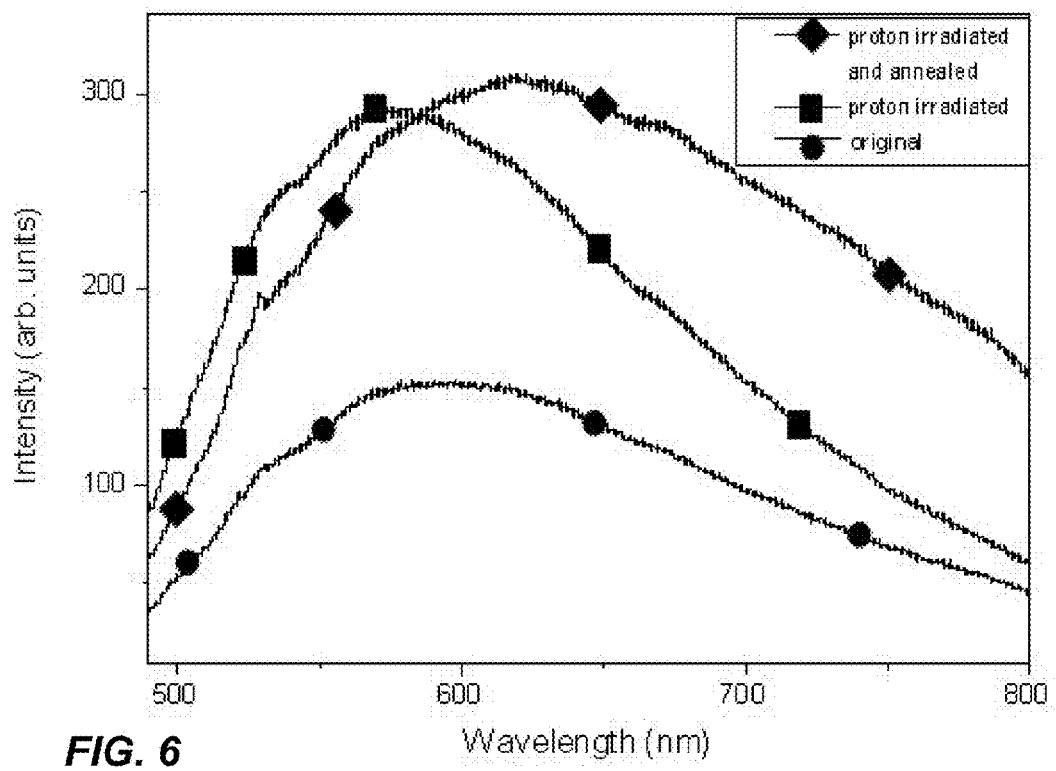
FIG. 6 depicts emission spectra for the functionalized DND-APES powder (original), powder irradiated at a dose $4.8\times10^{15}$ cm$^{-2}$ (proton irradiated) and irradiated and annealed at 600° C. powder (proton irradiated and annealed); excitation wavelength is 488 nm.

FIG. 6 illustrates PL spectra of functionalized ND-APES, irradiated ND-APES and further annealed (1 hr, 600° C.) sample. PL intensity was approximately twice increased due to irradiation and annealing. Thus this example demonstrates that proton irradiation of ND functionalized with Si-containing functional groups enhanced its PL intensity, although not very significantly. In example 3 it was demonstrated that the functionalization itself provided almost an order of magnitude enhancement of the PL intensity.

In similar experiments, DND was covered by PDMS shells and $SiO_2$ shells and these particles were irradiated with proton beam (fluence $4.8 \times 10^{15}$ protons $cm^{-2}$). About two times increase in PL intensity was also observed in fluorescent microscope, as compared to samples before irradiation.

Example 11

Controlling Nitrogen Content

Electron paramagnetic resonance (EPR) and electron spin echo (ESE) at high-frequency W-band (95 GHz) have been used to study defects in detonation nanodiamond and the possible presence of substitutional nitrogen in nanodiamonds of dynamic synthesis. The ESE-detected EPR spectra were measured using a two-pulse echo experiment with separation between the first and the second pulse. Two types of samples were studied. First sample, called ND I6 was produced from a mixture of TNT/RDX and further purified from $sp^2$ carbon and metals and fractionated down to 120 nm aggregate size. Average coherent scattering region size as obtained from XRD is 4 nm. Another sample, called RDDM, was obtained from a mixture of high energy explosive and non-diamond carbon (graphite), purified from $sp^2$ carbon and metals and fractionated down to 180 nm aggregate size. Average coherent scattering region sizes as obtained from XRD for this sample is around 10 nm. Sample RDDM has N content less than 0.5 wt %, as was obtained from C—H—N Carlo Ebra elemental combustion analysis, while sample ND I6 contains 2.4 wt % of nitrogen. Based on x-ray photoemission spectra (XPS), nitrogen content in RDDM sample is approximately 4-5 times less than in ND I6 sample.

The presence of substitutional N was easily detected at room temperature in the sample produced from mixture of graphite/RDX, while substitutional N is hardly detected in typical detonation ND even at low temperature.

The results of these experiments clearly demonstrate that the concentration of N as well as N state (substitutional) in ND of dynamic synthesis can be controlled at the stage of ND synthesis by, for a example, a proper choice of the precursor material. Not every type of detonation ND can be made photoluminescent through production of substitutional N during synthesis followed by production of NV centers by known means. However, the use of a mixture of explosives and carbon precursors, for example, facilitates formation of substitutional N in ND of dynamic synthesis.

Example 12

PL Enhancement: Treatment of Nanodiamond Soot to Create Optically-Active Structures In experiments below we demonstrate that nanodiamond particles and their aggregates may contains optically-active structures such as structures formed by non-diamond carbon atoms (presumably in amorphous, graphitic or other states) and show enhanced photoluminescence due to the presence of some residual $sp^2$ bonded carbon which, in addition, can be functionalized.

In this series of experiments as a starting material we used detonation soot obtained by detonation of a mixture of TNT/RDX in ice cooling media. Detonation soot was purified from metals and fractionated. Fractions with smaller sized soot particles were used for the experiment. This soot includes a mixture of diamond nanoparticles surrounded by non-diamond carbon. It also contains H, N and O elements in its composition presumably as parts of the surface terminal groups of soot particles. The initial sample was called soot1.

Figure 7:
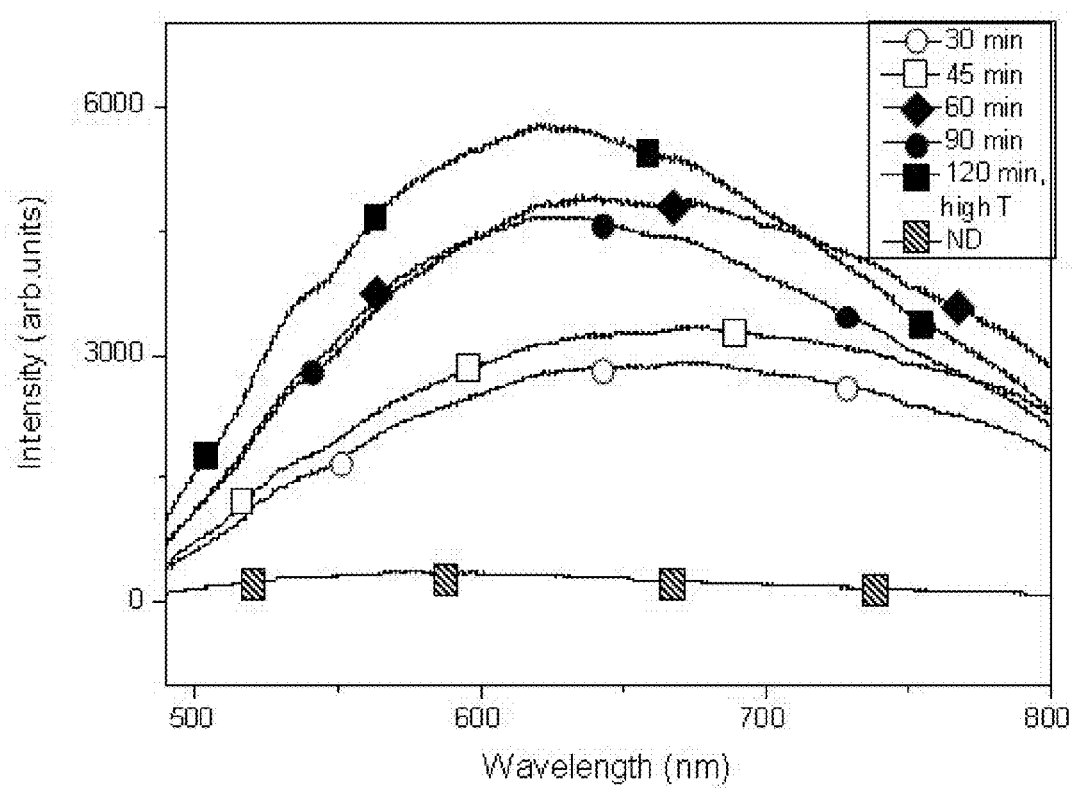
FIG. 7 depicts the PL spectra measured for typical DND I6 (control sample called ND) and for detonation soot heat treated in a mixture of sulfuric-nitric acids in a ratio of 3:1 for different times shown at the labels, wherein one of the samples was treated at higher temperature than others (ND 120 min); excitation wavelength is 488 nm.

200 mg of soot1 was placed in a flask along with 20 ml of 3 parts 96.4% of $H_2SO_4$ (from J. T. Baker) and 1 part 68-70% $HNO_3$ (from VWR), a 3:1 mixture. The sample was refluxed at a temperature of approximately 95° C. for 30 min, 60 min and 90 min. Both the residue and the supernatant were collected together and then separated after the treatment. After placing the collected reaction mixtures on a bench under a UV lamp, all three reaction mixtures demonstrated surprisingly strong luminescence. Then, samples were neutralized with NaOH and carefully washed with DI water multiple times until the residue acquired a high zeta potential (−45 mV) and part of the particles remained suspended in DI water. We also used a 3500 molecular weight membrane for the separation of residue and nanocarbon particles which were not attached to ND. The collected nanocarbon particles that went through the membrane had sizes less than approximately 1 nm as it was measured by photon correlation spectroscopy. The carefully washed ND (grayish color for pellets and amber color for the supernatant of ND which was colloidally stable) demonstrated a surprisingly strong PL when observed in an inverted fluorescent microscope. While the typical DND can be seen under green light excitation at approximately 1500 ms exposure time (with a ×60 magnification lens), the bright PL samples of the reaction products were seen at only 100-200 ms exposure time. The PL enhancement under illumination with UV and blue light was weak. FIG. 7 demonstrates 10 to 20 times enhancement of the PL intensity of the obtained samples as compared to the typical DND. It can be also concluded from FIG. 7 that it is possible to maximize PL emission by choosing time (and temperature) of treatment. Possibly it influences the sizes of PL nanocarbon species attached to DND. The Raman spectrum was weak due to high PL, but the presence of D and G graphite peaks were noticed. No photobleaching was observed during 20 min of irradiation during acquiring the spectra. A red shift of the peaks was observed for some samples in FIG. 7 and it can be hypothetically attributed to the activation of NV⁻ centers that are due to the passivation of the ND surface with nanographite islands. Inspection of the samples in high resolution electron microscope (HRTEM) indicated presence of graphite and amorphous carbon islands around ND particles several nanometers in size.

We produced fractions with an average particle size of about 50 nm, which can be further fractionated to smaller particle sizes. The initial soot can be milled (by dry or wet milling) and this would also facilitate the production of smaller luminescent ND-carbon dots structures.

We repeated the experiments by refluxing soot1 in a mixture of 5M $HNO_3$ (VWR) in DI water. After 3 days of treatment at 70° C. the soot remained black and the reaction mixture was not luminescent. This example demonstrates that this initial and typical treatment used for the production of carbon dots from candle soot did not occur. Furthermore, the carbon dots produced from candle soot required further passivation of their surfaces to generate photoluminescence of these particles. Passivation required chemical conjugation of the surface chemical groups using polyethylene glycol functionalities. Our observations using $H_2SO_4/HNO_3$ for the treatment and production of PL ND-nanocarbon structures are therefore unique and surprising. Further experiments below demonstrate different aspects of this finding.

Example 13

PL Enhancement is Time Stable

Detonation soot (Soot1) obtained by the detonation of a mixture of TNT/RDX by wet synthesis was purified from metals. Then the sample was heated for 2 hours in the mixture of $H_2SO_4/HNO_3$ in a proportion 3:1 at 140° C., after which time photoluminescent properties were observed. Two years later, the same sample was placed under a UV lamp and showed strong red luminescence observed by the naked eye. The spectra of this sample is shown in FIG. 7 (sample called 120 min high T). This example demonstrates that PL property acquired by the sample is stable in time.

Example 14

PL Enhancement: Physisorption of Carbon Dots

We were able to adsorb carbon dots, which were green in color, onto Ch-St-COOH (ND with negative zeta potential enriched with COOH groups) nanodiamonds by using high salt. To the carbon dot solution produced by treatment of micrographite in the mixture of sulfuric/nitric acids, nanodiamonds and high salt (20× concentrated saline-sodium citrate buffer) were added. The solid nanodiamond showed high PL with green excitation light under the microscope down to 500 ms exposure time. In this way, we screened the negative charges on the ND and carbon dot to cause the carbon dots to physisorb onto the ND particles.

Example 15

PL Enhancement: Time-Dependent Treatment of Different Carbon Samples

Below in Table I is a summary of experiments completed show the results of using acid treatment of nanoparticles at 130° C. along with the resulting solution color in white light and photoluminescence color as shown on a UV lamp. There is a time dependence on the evolution and retention of photoluminescence of the solutions (reaction mixtures). PL color on a UV lamp for a collected washed residue resuspended in water is denoted as (s).

TABLE I

Photoluminescent Nanocarbon Properties from Acid Treatment

| Carbon Source | Nitric acid 5M PL? | Sulf./ Nitric 3:1 PL? | Color of Solution | PL color, UV lamp time of treatment (min) |
|---|---|---|---|---|
| Soot 1 (wet synthesis, vendor 1) | N | Y | Grey | Red (s), 30<br>Y/Orange, 60<br>Yellow, 90<br>Red (s), 120 |
| Soot 2 (dry sythesis, vendor 2) | N | Y | Yellow<br>Grey | Yellow, 30<br>Yellow, 120 |
| Soot 3 (wet synthesis, vendor 3) |  | Y | Orange/Brown<br>Yellow/L. Brown<br>Grey | Dark Orange, 50<br>Orange, 90<br>White/Violet, 150<br>Purp./Viol., 3 h 20 m<br>No PL(s) 6 hrs |
| NanoNickel in carbon shell |  | Y | Yellow | Dark Orange, 15<br>Orange, 30<br>Light Orange, 35<br>Yellow, 40<br>Light Yellow, 45<br>Lighter Yellow, 50<br>Lighter Yellow, 60 |
| Micro-Graphite |  | Y | Colorless<br>Orange<br>Brown<br>Light Orange<br>Yellow<br>Light Yellow<br>Brown | None, 10<br>Lime Green,<br>Light pink, NaOH<br>Olive Green, 20<br>Blue/Green, 50<br>Bluer Green, 1 hr 20 m<br>Dark pink, NaOH |
| Poly 150 | N | Y | Yellow | Violet, 30<br>Violet, 90 |
| Poly 35 |  |  | Grey | Violet, 60 |
| Ch-St Yr 2008 | N | Y | Opaque White | Blue, 2 days<br>Purple, 5 hrs<br>No PL (s) |
| RuDDM Yr 2008 |  | Y | Opaque Yellow | Orange/yellow,<br>No PL (s) |
| OLC Dc-1 | N | Y | Yellow |  |
| OLC Da-1 |  | Y | Yellow | Yellow, 15<br>Dirty Yellow, 30 |
| OLC 1400 | N, 5 hrs |  |  |  |
| OLC 1450K |  | Y | Brown/Black + (s)<br>Brown/Black | Orange, 20<br>Green, 45 |
| OLC (hollow) | N | Y | Yellow | Orange, 30 |
| SWNT |  | Y | Yellow<br>Light yellow | Yellow, 30<br>(none), 60 |

(s) = solid particles

These examples include soot from different vendors (different conditions of detonation synthesis, different diamond content in the soot), onion-like carbon (OLC), ND produced from mixture of graphite and explosives (Poly, with high graphite content), and ND with amorphous carbon (Ch-St). Under these conditions, the solid particles of ~100 mg sample was refluxed in 10-20 mL of 3:1 Sulfuric-Nitric acid solution and aliquots from the sample were extracted at different time points.

Soot 1: Detonation synthesis product from vendor 1 (SKN, Snezinsk, Russia) produced using TNT/RDX mixture and wet cooling synthesis.

Soot 2: Detonation synthesis product from vendor 2 (000 Altai, Russia) produced using TNT/RDX mixture and dry cooling synthesis.

Soot 3: Detonation synthesis product from vendor 3 (Diamond Center, Sankt-Petersburg, Russia).

OLC Da-1: Onion-like carbon produced by annealing in vacuum of ND (ND obtained from Altai, Russia) at 1450K for 2 hours.
OLC Dc-1: Onion-like carbon produced by annealing in vacuum of ND (ND obtained from SKN, Snezinsk, fraction of ND 250 nm) at 1450K for 2 hours.
OLC 1450K: Onion like carbon obtained by annealing in vacuum at 1450K using I6 ND product.
Poly 150: nanodiamond synthesized from graphite/RDX by detonation synthesis with average size of 150 nm from vendor Feran, Moscow.
Poly 35: nanodiamond synthesized from graphite/RDX by detonation synthesis with average size of 35 nm from vendor Feran, Moscow.
Ch-St: nanodiamond purchased from New Technologies, Chelyabinsk, Russia. Micrographite: nominal size of 3 microns from Aldrich.
RDDM: nanodiamond from vendor Real Dzerzinsk, Russia. Synthesized from a mixture of graphite/RDX.
Nanonickel in carbon shell: nickel embedded in an $sp^2$ carbon shell from Ekaterinburg State Technical University.
SWNT: Single walled nanotube from Nanotechnologies, Clemson, S.C.
Inspection under fluorescent microscope of 3 types of soot (soot1, soot2 and soot3) treated under identical conditions indicated that most bright PL was obtained when soot 1 was used as a starting material for production of PL ND-nanocarbon.

Example 16

PL Enhancement: Decomposition of Onion Like Carbon Containing ND Core

Onion-like-carbon, Da-1 (with a nanodiamond core), was treated under refluxing conditions in sulfuric/nitric acid in a 3:1 ratio and it was found that after 15 min of reaction at 130° C., the supernatant was luminescent orange in color under a UV lamp. The $sp^2$ carbons on onions are degraded, forming nanocarbon structures that give rise to photoluminescence of the orange color. The orange color may also include green carbon nanostructures. Separating the NDs from the supernatant and washing the NDs caused a loss of photoluminescence of the residue particles produced under this condition.

Example 17

Chemically Conjugated NDs with Carbon Dots

We propose a mechanism to attach carbon dots to the surface of nanodiamonds using amide coupling reactions, whereby the carboxylate moieties on both particles are coupled through a diamine compound. To a dried suspension of carbon dots an anhydrous solution of dimethylformamide will be added along with carboxylated nanodiamonds. To this solution, a diamine compound will be added along with coupling reagents, such as EDC ethylenedicarbodiimide. The reaction will create a diamide link between the nanodiamonds and carbon dots.

Example 18

Treatment Results of Soot 3

Soot3 produced by wet detonation synthesis from a mixture of TNT/RDX (water cooling media, 60 wt % of ND in the soot) was refluxed in 3:1 sulfuric (96.4%)/nitric acid (68-70%) at 130° C. and probes at different time points were taken from the reaction solution. After 50 minutes and 110 minutes, the reaction mixture appeared orange luminescent under a UV lamp. After diluting these solutions, followed by sedimentation of the nanoparticles, the suspension showed green color photoluminescence under the UV lamp. Upon resuspension of the particles, these diluted solutions were light yellow in color. This suggests that the most colloidally stable carbon dot particles are green and the less stable particles are orange. The reaction after 155 minutes showed no orange photoluminescence, but was purple/blue in photoluminescence. Thus, demonstrating that extended refluxing conditions may eliminate the orange and green photoluminescent species, as expected by further decomposition of carbon structures, also called over-etching. Inspection under microscope of washed residue indicated that PL ND-nanocarbon structures were formed. After treatment of soot3 during 6 hrs and washing residue, ND was not luminescent (PL non-diamond carbon was all oxidized).

Example 19

Treatment Results of Soot2

For Soot 2 (dry synthesis in $CO_2$ cooling media, 35 wt % of ND in the soot), the solid was treated with refluxing 3:1 sulfuric/nitric acid at 130° C. and the supernatant showed yellow photoluminescence on the UV lamp after 30 and 40 minutes. After a reaction of 120 minutes, the suspension of residue lost all photoluminescence. In another similar experiment, soot2 was treated 1 hr at 130° C. and then 20 min at 200° C. After treatment, residue looked white. Inspection in fluorescent microscope of the washed residue did not reveal PL properties. This example shows that depending on the detonation soot and conditions of the treatment a sample can be over-etched (nanocarbon on ND surface completely oxidized) and PL properties can not be obtained.

Example 20

Treatment of Poly 35 Nanodiamond

Poly 35 (ND produced from mixture of graphite and explosive) was treated with 3:1 sulfuric:nitric acid solution under reflux at 130° C. and after 60 minutes the reaction mixture solution appeared to have violet photoluminescence. The collected supernatant showed green photoluminescence. No yellow photoluminescence was observed.

Example 21

Treatment of Ch-St Nanodiamond

As-received from a vendor Ch-St DND (purified from soot at a vendor site using a mixture of sulfuric acid and chromic anhydride; it contains about 2 wt % residual $sp^2$ phase DND) was treated in 3:1 sulfuric: nitric acid under reflux conditions at 70.0 during 3 days (a typical carboxylation/oxidation reaction described in the literature such as, for example in Huang, L. C. L.; Chang, H. C. Langmuir 2004, 20, 5879) and no photoluminescence was observed in supernatant or the ND. Further treatment at higher temperature (90° C.) did not produce PL DND either. The zeta potential remained positive throughout the reaction.

Example 22

Treatment of NanoNickel

Ni@C (2 nm nano-nickel particles surrounded by nm-thick amorphous carbon layer) was treated in 3:1 sulfuric:

nitric acid at 130° C. and monitored over time under reflux. A color change was seen from orange to light yellow over a period of 15 to 60 minutes.

Example 23

Treated Soot1 Resists Photobleaching

Figure 8:
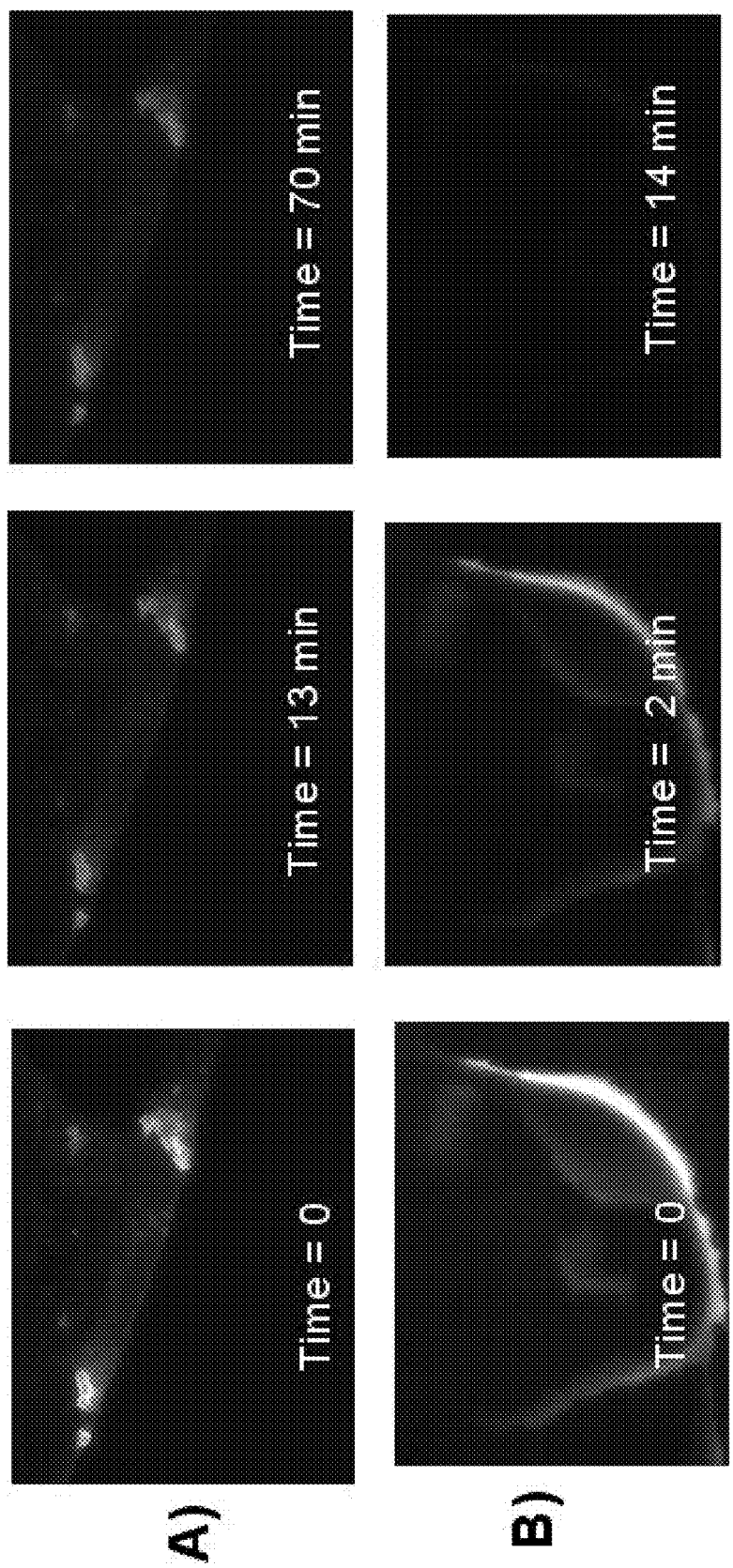
FIG. 8 depicts a series of photos (A—top row) and (B—bottom row) of time lapse photos of a sample of supernatant of 3:1 sulfuric-nitric acids treated Soot 1 (A) and TAMRA fluorophore dye (B) during irradiation with green excitation light. Sulfuric-nitric acid treated Soot 1 photobleaches more slowly than TAMRA.

A low degree of photobleaching for treated in the mixture of sulfuric/nitric acids Soot 1 is observed. Approximately 50% photobleaching seen after 70 minutes of supernatant collected after reaction irradiated with green excitation light (FIG. 8). As compared to TAMRA organic fluorophore, TAMRA photobleaches completely in 14 minutes. This suggests that the photoluminescent species in supernatant is not molecular in structure, but probably is rather a particle-based species with quantized energy.

Example 24

Control Experiment with HPHT Nanodiamond

The treatment of high pressure high temperature (HPHT) nanodiamonds with the 3:1 sulfuric-nitric acid under reflux at 130° C. did not produce any observable PL species, which suggests that nondiamond carbon contributes to the PL observed.

Example 25

Treating Carbon Fibers Produces PL Species

The treatment of vapor grown carbon fibers with 3:1 refluxing sulfuric-nitric acid at 130° C. produced a yellow/orange and a yellow/green supernatant over 10-30 min and 60 minutes, respectively.

Example 26

Treatment of Micrographite Produces PL Species and Combining them with DND

Boiling of 250 mg of micrographite in a 20 ml volume of 3:1 sulfuric/nitric acid for 20 minutes produced a yellow PL solution, as seen on the UV lamp. This solution was separated from solid graphite by centrifugation. To the yellow PL solution, 1 gram of nanodiamond powder was added (I6 DND with positive zeta potential +45 mV). Refluxing began again for 30 minutes and the solid was centrifuged to remove the unreacted, yellow PL solution (pH 1). The ND solid was washed by centrifugation 3 times (pH 3), followed by sonication for 30 sec and subsequent washing, producing a ND solution of pH 5. None of the washings showed yellow PL. The ND solid showed intense PL at 500 ms under green excitation light of the inverted fluorescence microscope. Thus the PL carbon species/nanoparticles were attached to the ND during this procedure and imparted/activated in ND PL property.

Figure 9:
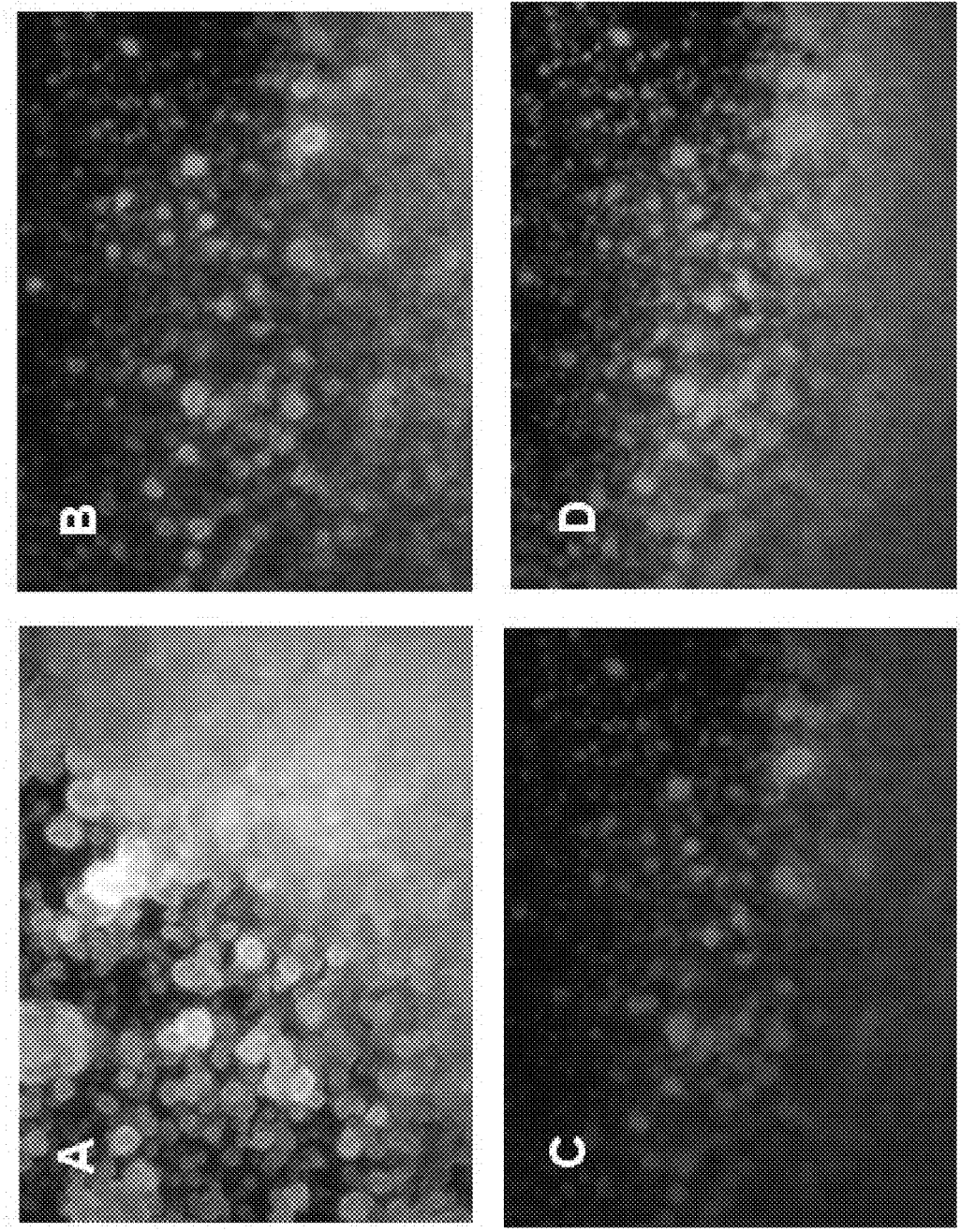
FIG. 9 depicts a series of photos (A-D) showing nanodiamond solid photoluminescence. Initially, micrographite was refluxed for 20 minutes in 3:1 sulfuric-nitric acids. The supernatant of that mixture was then subsequently refluxed for 30 minutes after the addition of I6 DND powder. The nanodiamond was washed with DI water by removing the supernatant after pelleting the nanodiamond after centrifugation. The photoluminescence of the nanodiamond is shown illuminated from green excitation light after 1 wash (A) and after 5 washes (B), as compared to PL from blue excitation light (C), and UV excitation light (D) with all photos taken with 1500 ms exposure using a 60× objective.

FIG. 9 depicts a series of photos (A-D) showing nano-diamond solid photoluminescence from reaction of graphite solution with I6 DND; the photoluminescence of the nanodiamond is shown in green excitation light after 1 wash (A) and after 5 washes (B), as compared to PL from blue excitation light (C), and UV excitation light (D) with all photos taken with 1500 ms exposure using a 60× objective.

In a similar approach, DND with positive and negative zeta potentials were mixed with PL nanocarbon structures obtained by treatment of micrographite. Samples were sonicated and then washed 3-4 times until supernatant showed no PL on UV lamp. During inspection in the fluorescent microscope it was observed that PL nanocarbon was adsorbed on DND with positive zeta potential, making it luminescent, while no luminescence was observed for DND with negative zeta potential.

Example 27

Temperature Dependence on PL Species Production

In a series of experiments, detonation soot1 was treated at equal conditions (amount of reagents and duration of treatment), but at different temperatures: 70, 80, and 90° C. The residue was carefully washed and inspected in fluorescent microscope. It was concluded that treatment at approximately 80° C. and above is needed to produce PL ND-containing structures.

From these experiments one can readily determine that the PL of ND particles and agglomerates thereof can be enhanced by at least a factor of 2 to 3 and often by orders of magnitude such that increases of PL of greater than or equal to 10-20 times can be obtained.

In accord with certain embodiments consistent with the present invention, photoluminescent nanodiamond particles have enhanced photoluminescent properties produced as a result of minimizing the nitrogen content of impurities or imperfections in the nanodiamond lattice and by location of photoluminescent structures on the outer surface of the nanodiamond particles. This inhibits absorption of emission and enhances the intensity of the emission.

Figure 10:
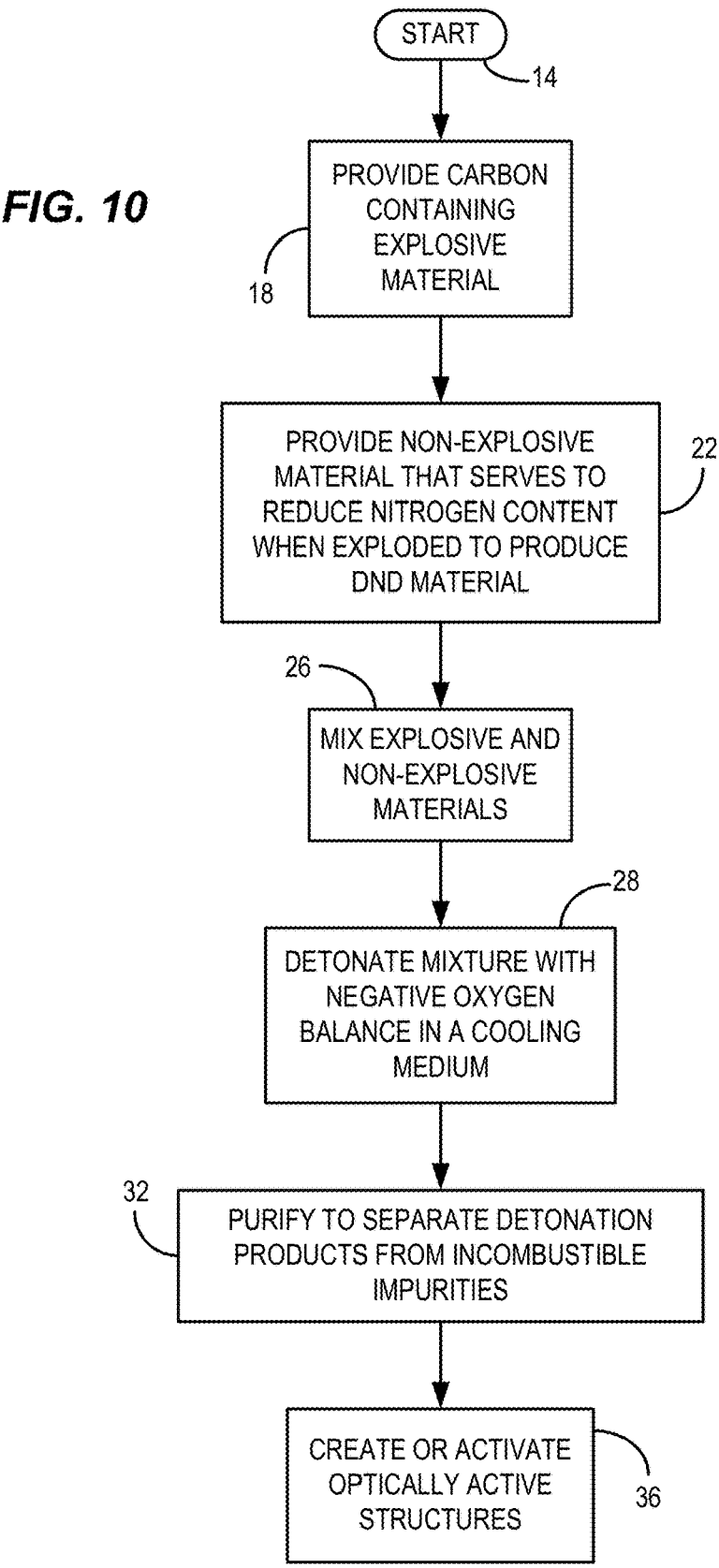
FIG. 10 is an example flow chart of a process consistent with certain embodiments of the present invention.

Turning now to FIG. 10, starting at 14, we can conclude that a method of manufacturing of photoluminescent nanodiamond-containing material involves providing at least one type of carbon-containing explosive material at 18 and at least one type of non-explosive material at 22, wherein the non-explosive material helps to reduce the nitrogen content in the nanodiamond-containing material and/or to dope the nanodiamond-containing material with other than nitrogen elements. The materials are mixed at 26 and the mixture is detonated at 28 under conditions with negative oxygen balance in a cooling medium. The process then proceeds to 32 where the product of detonation is purified to remove the incombustible impurities. At 36, additional processing is carried out for creation, activation, or enhancement of optically active structures.

In certain implementations at 36, the additional processing includes treatment in the mixture of sulfuric and nitric acids creating non-diamond carbon structures covering at least part of nanodiamond surface and possessing optically active properties themselves or activate the optical properties of the imperfections in the nanodiamond crystal lattice. In certain implementations, additional processing includes the purification from non-diamond carbon and additional treatment that provides vacancies, including irradiation with electron beam, ion beam, or positron beam followed by annealing. In certain implementations, at least one type of explosive material is from the following: trinitrotoluene, hexogen, hexanitrostilbene, benzotrioxofuraxan, triamino-trinitrobenzene or other carbon-containing explosives, and where a combination of explosives is chosen to minimize the nitrogen content in the lattice of nanodiamond particles. In certain implementations, at least one type of non-explosive material is from the following: non-diamond carbon, graphite, soot, carbon black, hydrocarbons, doped non-diamond carbon, doped graphite, doped soot, doped carbon black, intercalated non-diamond carbon, intercalated graphite, intercalated soot, intercalated carbon black, silicon carbide, silicone-containing compounds, silane(s), silicides, carbides, metal-containing compounds, and wherein at least one dopant atom or intercalated element atom is incorporated into diamond lattice. In certain implementations, elements for doping and/or intercalation of the non-explosive material are selected from: N, Si, Ni, and Cr. In certain implementations, the cooling media contains Si-atom containing compounds. In certain implementations, the Si-related compounds include silane.

Thus, in accord with certain embodiments consistent with the present teachings, a nanodiamond-containing material has nanodiamond particles or aggregates thereof containing optically-active structures, the particles having a core and a surface. The nanodiamond-containing material provides enhancement of the intensity of photoluminescent emission at least a factor of two as compared to the photoluminescence of nanodiamond particles or their aggregates not containing the optically active structures. The optically-active structures are located outside of the nanodiamond core and the optically-active structures have non-diamond carbon structures covering at least part of the nanodiamond surface.

In certain materials, the non-diamond carbon structures contain functional groups terminating at least a portion of their carbon surface atoms. In certain materials, the non-diamond carbon structures comprise nanographite. In certain materials, the size of nanographite particles is less than approximately three nanometers. In certain materials, the size of nanographite particles is less than approximately one nanometer. In certain materials, the spectrum of the emission is determined in part by the size of nanographite particles. In certain materials, the nanodiamond-containing material is in a solution and wherein the spectrum of the emission is determined in part by the pH of the solution containing the nanodiamond-containing material. In certain materials, the functional groups contain nitrogen, nitrogen oxides or nitronium ion. In certain materials, the functional groups contain carboxylic groups. In certain materials, the non-diamond carbon structures are covalently bonded with the nanodiamond core. In certain materials, the non-diamond carbon structures comprise nanographite particles.

In certain materials, the nanographite particles are attached to the nanodiamond core by carbon-carbon bonds. In certain materials, the nanographite particles are attached to the nanodiamond core by carbon-nitrogen or carbon-oxygen bonds. In certain materials, the nanographite particles attached to the nanodiamond core are obtained by treatment of graphite containing material and nanodiamond particles by exposure to a mixture of sulfuric and nitric acids. In certain materials, the nanographite particles attached to the nanodiamond core are obtained by treatment of nanodiamond soot in a mixture of sulfuric and nitric acids. In certain materials, the nanographite particles attached to the nanodiamond core are obtained by treatment of graphite containing material in a mixture of sulfuric and nitric acids followed by mixing with nanodiamond particles. In certain materials, the nanographite particles are less than approximately three nanometers in size. In certain materials, the nanographite particles are less than approximately one nanometer in size.

In certain materials, the non-diamond carbon structures bonded to the nanodiamond core are obtained by treatment in a mixture of sulfuric and nitric acid of nanodiamond particles and at least one of detonation soot, other soot, carbon onions, graphite, micrographite, nanographite, carbon nanotubes, carbon nanohorns, carbon fibers or other non-diamond carbon structures. In certain materials, the treatment in a mixture of sulfuric and nitric acid includes: taking at least one of detonation soot, other soot, carbon onions, graphite, micrographite, nanographite, carbon nanotubes, carbon nanohorns, carbon fibers or other non-diamond carbon structures; stirring in a mixture of sulfuric and nitric acids at temperature exceeding approximately 80 degrees Celsius; collecting the supernatant and mixing with nanodiamond particles; and exposing the mixture to a temperature exceeding approximately 80 degrees Celsius. In certain materials, the non-diamond carbon structures are chemically bonded with the nanodiamond core through linkages including bonds of carbon-carbon, ether, ester, imides, thiourea, urea, and amides.

In certain materials, the non-diamond carbon structures are not covalently bonded to the nanodiamond core. In certain materials, non-diamond carbon structures comprise nanographite particles. In certain materials, the nanographite particles are attached to the nanodiamond core by van der Waals bonding. In certain materials, the nanographite particles are attached to the nanodiamond core by ionic bonding. In certain materials, the non-diamond carbon structures also contain atoms other than carbon. In certain materials, the non-diamond carbon structures are created by treatment of detonation soot. In certain materials, the treatment of detonation soot includes treatment in a mixture of sulfuric and nitric acids. In certain materials, the mixture of sulfuric and nitric acids contains nitric acid between 1/10 and 9/10 parts. In certain materials, the treatment in a mixture of sulfuric and nitric acids is carried out at a temperature exceeding approximately 80 degrees Celsius. In certain materials, the treatment in a mixture of sulfuric and nitric acids is carried out at a temperature exceeding approximately 90 degrees Celsius.

In certain materials, the non-diamond carbon structures are created by treatment of the nanodiamond-containing material comprised of nanodiamonds surrounded by non-diamond carbon. In certain materials, the nanodiamonds that are surrounded by non-diamond carbon are obtained by heating nanodiamond in an inert atmosphere or vacuum at a temperature exceeding 900 degrees Celsius. In certain materials, the treatment includes treatment in a mixture of sulfuric and nitric acids. In certain materials, the nanodiamonds surrounded by non-diamond carbon material are produced by mechanical mixing of the nanodiamonds and non-diamond carbon.

In certain materials, the enhancement of the intensity of photoluminescence is at least five times as compared to the photoluminescence of nanodiamond particles and their aggregates not containing optically-active non-diamond carbon structures covering at least part of nanodiamond surface. In certain materials, the nanodiamond particles or agglomerates are produced by the detonation of explosives. In certain materials, the nanodiamond particles or agglomerates are produced by the detonation of a mixture of at least one non-diamond carbon precursor and at least one type of explosive. In certain materials, the spectrum of photoluminescence is dependent upon the pH of the suspension of the nanodiamond-containing material.

Consistent with certain of the present teachings, a nanodiamond-containing material has nanodiamond particles containing optically-active structures providing enhancement of the intensity of photoluminescence of at least two times as compared to the photoluminescence of nanodiamond particles not containing the optically-active structures. The nanodiamond particles have a core comprised of crystallographic lattice. The optically-active structures include imperfections in the diamond crystallographic lattice; and optically-active structures located outside of the nanodiamond core; where the enhancement of photoluminescence is a result of both the imperfections and the optically-active structures.

In certain materials, the structures located outside of the nanodiamond core include non-diamond carbon structures covering at least a part of nanodiamond surface. In certain materials, the non-diamond carbon structures are covalently bonded to nanodiamond surface. In certain materials, the imperfections in the diamond crystallographic lattice include at least one of substitutional or interstitial nitrogen, nitrogen atoms complexes, nitrogen atom(s) complexes with vacancy(s), vacancies, substitutional or interstitial Si atom, Si atom(s) complexes with vacancy(s), metal-containing complexes, point, linear and planar defects, and combinations thereof. In certain materials, the structures located outside of the nanodiamond core comprise surface structures preventing charge transfer from said imperfections in the diamond crystallographic lattice so that the optical activity of the imperfections is preserved. In certain materials, the surface structures include surface functional groups. In certain materials, the surface structures include non-diamond carbon structures covering at least a part of nanodiamond surface. In certain materials, the structures located outside of the nanodiamond core are created by an oxidative treatment of starting material comprising nanodiamonds surrounded by non-diamond carbon, where the non-diamond carbon is selected from detonation soot, carbon onions with nanodiamond core, mechanical and/or chemical mixture of nanodiamond particles and non-diamond carbon. In certain materials, the oxidative treatment of starting material includes treatment in a mixture of sulfuric and nitric acid.

In certain materials, the surface structures are covered by a high refractive index media that reduces losses due to light scattering. In certain materials, enhancement of the intensity of photoluminescence is at least five times as compared to the photoluminescence of nanodiamond particles or their aggregates not containing the optically-active structures. In certain materials, nanodiamond particles are produced by detonation of explosives. In certain materials, nanodiamond particles are produced by detonation of a mixture of at least one non-diamond carbon precursor and at least one type of explosives.

Certain nanodiamond-containing material consistent with certain of the present teachings, have a nanodiamond particle produced by dynamic synthesis and having a core comprising of a crystallographic lattice. The nanodiamond particle contains imperfections in the diamond crystallographic lattice. The nanodiamond particle has a crystal size larger than approximately 10 nanometers. The nanodiamond particle demonstrates enhancement of the intensity of photoluminescence at least two times as compared to the photoluminescence of a nanodiamond particle with crystal size less than approximately 10 nanometers.

In certain materials, the nanodiamond material contains a plurality of nanodiamond particles and other material; and the plurality of nanodiamond particles have a crystal size larger than approximately 10 nanometers comprise more than 30% of nanodiamond material by volume. In certain materials, imperfections in the diamond crystallographic lattice include complexes of nitrogen atom(s) and vacancies, and the nanodiamond particle is produced by detonation of explosives. In certain materials, the nanodiamond particle has a crystal size larger than approximately 20 nanometers. In certain materials, the nanodiamond particle has a diamond peak of 1332 $cm^{-1}$ in the Raman spectra. In certain materials, the nanodiamond particle has a crystal size large enough to prevent charge transfer to surface charge acceptors. In certain materials, imperfections in the diamond crystallographic lattice include complexes of silicon atom(s) and vacancies. In certain materials, the nanodiamond particle is produced by detonation of explosives mixed with non-diamond carbon precursors.

A nanodiamond-containing material consistent with certain of the present teachings has nanodiamond particles having a surface and containing optically-active structures. The nanodiamond-containing material provides enhancement of the intensity of photoluminescence by at least two times that compared to the photoluminescence of nanodiamond particles that do not contain the optically active structures. The optically-active structures are located on the surface of nanodiamond particles and include silicon structures containing silicon atoms or silicon containing functional groups. In certain materials, the silicon structures further include inorganic compounds and/or organic compounds. In certain materials, the silicon structures contain organic compounds including aminopropyltriethoxysilane, tricosane silane, phenyl dimethyl silane whereby the silicon atom contains a silicon ester, or an oxygen bridge Si-OR, where the R group is composed of an organic moiety. In certain materials, the silicon structures contain silica-inorganic compounds and wherein the silica-inorganic compounds include silica made of $SiO_2$, or other combinations of SiOR, where R is an inorganic compound, including silicon, zirconium, aluminum, or magnesium.

In certain materials, the silicon structures include silicon atom in combination with an organic or inorganic compound that contains a silicon-carbon bond or SiR, where R is an organic moiety. In certain materials, the silicon structures include a compound of the formula R3SiO— with at least one oxygen atom is siloxanes, where R is oxygen or an organic moiety. In certain materials, the photoluminescence intensity is enhanced by exposure of the nanodiamond containing material having the silicon structures to high energy irradiation, including electron, proton, or other ion beam irradiation. In certain materials, the optically-active structures further include imperfections in the diamond crystallographic lattice. In certain materials, the optically-active structures are located on at least a part of the nanodiamond surface. In certain materials, the enhancement of the intensity of photoluminescence is at least five times the photoluminescence of nanodiamond particles and their aggregates that do not contain silicon structures. In certain materials, the nanodiamond particles are produced by the detonation of explosives. In certain materials, the nanodiamond particles are produced by the detonation of a mixture of at least one non-diamond carbon precursor and at least one type of explosive. In certain materials, the nanodiamond particles are produced by the detonation of a mixture of at least one inorganic material, including silicon, nickel, chromium, tungsten, cobalt, tantalum, titanium, and at least one type of explosive.

While certain illustrative embodiments have been described, it is evident that many alternatives, modifications, permutations and variations will become apparent to those skilled in the art in light of the foregoing description.

What is claimed is:

1. Nanodiamond material, comprising:
    nanodiamond particles containing optically-active structures providing enhancement of the intensity of photoluminescence as compared to the photoluminescence of nanodiamond particles not containing the optically-active structures;
    the nanodiamond particles having a core comprised of diamond crystallographic lattice and a surface;

where said optically-active structures comprise:
  at least one imperfection in the diamond crystallographic lattice, and
  at least one optically-active structure located outside of the nanodiamond core comprising non-diamond carbon islands on the surface of the nanodiamond particle;
whereby, the enhancement of photoluminescence is a result of both the imperfections in the diamond crystallographic lattice in the core of each nanodiamond particle and the optically-active structures located outside of the nanodiamond core.

2. The nanodiamond material according to claim 1, where the optically-active structures located outside of the nanodiamond core further comprise non-diamond carbon structures covering at least a part of the nanodiamond surface.

3. The nanodiamond material according to claim 2, where the non-diamond carbon structures are bonded to the nanodiamond surface through covalent, ionic or van der Waals bonding.

4. The nanodiamond material according to claim 2, where the optically-active structures located outside of the nanodiamond core are created by an oxidative treatment of starting material comprising nanodiamonds surrounded by non-diamond carbon, where the non-diamond carbon is selected from the group consisting of detonation soot, carbon onions, carbon onions with nanodiamond core, graphite, micrographite, nanographite, carbon nanotubes, carbon nanohorns, carbon fibers, non-diamond carbon structures, and mechanical or chemical mixtures of nanodiamond particles and non-diamond carbon.

5. The nanodiamond material according to claim 4, where the oxidative treatment of starting material further comprises treatment in a mixture of sulfuric and nitric acid.

6. The nanodiamond material according to claim 2, where the optically-active structures located outside of the nanodiamond core comprise non-diamond carbon structures or surface groups covering at least a part of the nanodiamond surface.

7. The nanodiamond material according to claim 2, where a size of the non-diamond carbon structures controls emission color.

8. The nanodiamond material according to claim 1, where the imperfections in the diamond crystallographic lattice include at least one of substitutional or interstitial nitrogen, nitrogen atoms complexes, nitrogen atom, nitrogen atoms complexes with one or more vacancies, interstitial carbon atoms, vacancies, substitutional or interstitial Si atom, Si atoms complexes with one or more vacancies, metal-containing complexes, linear and planar defects, or combinations thereof.

9. The nanodiamond material according to claim 1, where the optically-active comprises surface functional groups.

10. The nanodiamond material according to claim 9, where the optically-active structures located outside of the nanodiamond core comprise surface structures preventing charge transfer from said imperfections in the diamond crystallographic lattice so that the optical activity of the imperfections is preserved.

11. The nanodiamond material according to claim 1, where the optically-active structures are covered by a high refractive index media that reduces losses due to light scattering.

12. The nanodiamond material according to claim 1, where the nanodiamond particles are produced by detonation of explosives.

13. The nanodiamond material according to claim 1, where the nanodiamond particles are produced by detonation of a mixture of at least one non-diamond carbon precursor and at least one type of explosive.

14. The nanodiamond material according to claim 13, where the nanodiamond particles are produced by detonation of a mixture of at least one non-diamond carbon precursor and at least one type of explosive, and
  where at least one type of non-diamond carbon precursor is selected from the group consisting of: non-diamond carbon, graphite, soot, carbon black, hydrocarbons, doped non-diamond carbon, doped graphite, doped soot, doped carbon black, intercalated non-diamond carbon, intercalated graphite, intercalated soot, intercalated carbon black, silicon carbide, silicone-containing compounds, silane(s), silicides, carbides and metal containing compounds, and
  where at least one dopant atom or intercalated element atom is incorporated into the diamond lattice.

15. The nanodiamond material according to claim 14, an comprising elements for doping or intercalation of the non-explosive material selected from the group consisting of N, Si, Ni, and Cr.

16. The nanodiamond material according to claim 1, where photoluminescence is caused by light excitation wavelengths in the green, blue, or UV regions of the spectrum.

17. The nanodiamond material according to claim 1, where the optically-active structures located outside of the nanodiamond core comprise surface groups that are present as a result of synthesis, purification, or modification, species adsorbed from the environment, species forming solvation shells or solid-state shells, partial shells around the nanodiamond particle, discrete functional conjugates, or nitronium ions or combinations thereof.

18. The nanodiamond material according to claim 17, where the optically-active structures located outside of the nanodiamond core comprises: polymer shells, silica shells, metal shells, oxide shells, silicon or germanium shells, and organic or inorganic shells.

19. The nanodiamond material according to claim 1, where the optically-active structures located outside of the nanodiamond core are generated by:
  annealing the nanodiamond particles in vacuum or inert gas at a temperature range 700° C. to 1400° C., and
  treating the nanodiamond particles with an oxidizing agent.

20. The nanodiamond material according to claim 1, where the nanodiamond particles have surface terminations comprising siloxane groups having functionalities with an —O—Si backbone chemical structure, silane groups having functionalities with a —Si backbone chemical structure, a polydimethylsiloxane (PDMS) or a siloxane shell.

21. The nanodiamond material according to claim 1, where the nanodiamond particles are produced by detonation of explosives containing at least one element which induces color centers.

22. The nanodiamond material according to claim 21, where the nanodiamond particles exhibit optical, magnetic, and electrical properties not present in nanodiamond particles not containing the at least one element which induces color centers.

23. The nanodiamond material according to claim 1, where the nanodiamond particles are produced by detonation of explosives followed by cooling in cooling media, and where the cooling media contains at least one element which induces color centers in nanodiamond particle core.

24. The nanodiamond material according to claim 1, where the optically active structures comprise at least one diagnostic or therapeutic agent.

25. The nanodiamond material according to claim 1, comprising nanodiamond particles produced using a laser for phase conversion of carbon precursors containing nitrogen, and further comprising nanodiamond with controlled nitrogen content.

26. The nanodiamond material according to claim 1, where the nanodiamond particles comprise nanodiamond particles produced from synthetic high-pressure high-temperature or natural diamonds.

27. The nanodiamond material according to claim 1, where the imperfections in the diamond lattice are produced by irradiation of nanodiamond powder or nanodiamond suspension in a liquid by electron, proton, ion, alpha or gamma radiation.

28. The nanodiamond material according to claim 27, where the nanodiamond particles are annealed and purified.

29. The nanodiamond material according to claim 1, comprising the nanodiamond particles with a surface in contact with a solvent or other environment preventing the formation of a positive charge on complexes formed by nitrogen atoms and internal defects whereby photoluminescence is enhanced.

30. The nanodiamond material according to claim 1,
where the optically active structures located outside of the nanodiamond core comprises silicone-containing compounds; and
where the silicone-containing compounds further comprise:
aminopropyltriethoxysilane, tricosane silane, phenyl dimethyl silane, alkoxysilanes, polysiloxane, silica, or SiOR compound where R is an inorganic species, including but not limited to silicon, zirconium, aluminum, and/or magnesium; or
silicon atom in combination with a compound that contains a silicon-carbon bond or, silazanes or organosilanes; or
silicon atom containing compounds of the formula X3SiO— with at least one oxygen atom where the X group may be of oxygen, or an inorganic group containing carbon.

31. The nanodiamond material according to claim 1, comprising the nanodiamond particles covered by PDMS shell or $SiO_2$ shell irradiated with electron, proton, ion, alpha or gamma-radiation.

32. The nanodiamond material according to claim 1, where the material is affixed to or mixed with an item that is to be marked, imaged or tagged; whereby, presence of the material is detectable by inducing photoluminescence of the nanodiamond particles by excitation with light of a prescribed wavelength.

33. The nanodiamond material according to claim 32, where the item to be marked, imaged or tagged comprises gunpowder or explosives.

34. The nanodiamond material according to claim 1, where the material is introduced into biological matter for use as a cellular tracer, bio-label, bio-tag, bio-sensor or chemical sensor; whereby a presence of the material is detectable by inducing photoluminescence of the nanodiamond particles by excitation with light of a prescribed wavelength.

35. The nanodiamond material according to claim 1, further comprising a diagnostic or therapeutic agent attached to at least one of the surfaces.

* * * * *